US012110471B2

(12) United States Patent
Dayton et al.

(10) Patent No.: US 12,110,471 B2
(45) Date of Patent: *Oct. 8, 2024

(54) ENZYMATIC REMOVAL OF CHLOROPHYLL SUBSTRATES FROM TRIACYLGLYCEROL-BASED OILS

(71) Applicant: Bunge Global Innovation, LLC, Chesterfield, MO (US)

(72) Inventors: Christopher Loren Gene Dayton, Jupiter, FL (US); Arjen Sein, Echt (NL); Evert Tjeerd Van Rij, Echt (NL); Jan Metske Van Der Laan, Echt (NL)

(73) Assignee: Bunge Global Innovation, LLC, Chesterfield, MO (US)

( * ) Notice: Subject to any disclaimer, the term of this patent is extended or adjusted under 35 U.S.C. 154(b) by 103 days.

This patent is subject to a terminal disclaimer.

(21) Appl. No.: 17/819,652

(22) Filed: Aug. 15, 2022

(65) Prior Publication Data

US 2022/0380700 A1 Dec. 1, 2022

Related U.S. Application Data

(63) Continuation of application No. 16/650,599, filed as application No. PCT/EP2018/076130 on Sep. 26, 2018, now Pat. No. 11,447,714.

(60) Provisional application No. 62/736,126, filed on Sep. 25, 2018, provisional application No. 62/736,129, filed on Sep. 25, 2018.

(30) Foreign Application Priority Data

Sep. 26, 2017 (EP) .................................... 17193211

(51) Int. Cl.

| | |
|---|---|
| ***C12N 9/16*** | (2006.01) |
| ***C11B 3/00*** | (2006.01) |
| ***C12N 9/18*** | (2006.01) |

(52) U.S. Cl.

CPC ................ *C11B 3/003* (2013.01); *C12N 9/18* (2013.01); *C12Y 301/01014* (2013.01); *C12Y 301/04003* (2013.01)

(58) Field of Classification Search

CPC . C12N 9/16; C12N 9/18; C12P 17/182; C12P 7/04

See application file for complete search history.

(56) References Cited

U.S. PATENT DOCUMENTS

| | | | |
|---|---|---|---|
| 11,098,265 B2 * | 8/2021 | Dayton | .............. B01J 20/28069 |
| 11,447,714 B2 * | 9/2022 | Dayton | .................... C12N 9/18 |
| 2012/0149927 A1 | 6/2012 | Soe et al. | |

FOREIGN PATENT DOCUMENTS

| | | |
|---|---|---|
| WO | 2011110967 A1 | 9/2011 |
| WO | 2013160372 A1 | 10/2013 |

OTHER PUBLICATIONS

Matsumoto et al., “Comprehensive Sequence Analysis of 24,783 Barley Full-Length cDNAs Derived from 12 Clone Libraries”, Plant Physiology, May 2011, vol. 156, pp. 20-28.

The International Barley Genome Sequencing Consortium: “A physical, genetic and functional sequence assembly of the barley genome”, Nature, Nature, 2012, vol. 491, pp. 711-716.

International Search Report and Written Opinion for PCT/EP2018/076130, mailed on Nov. 13, 2018, 12 pages.

* cited by examiner

*Primary Examiner* — Tekchand Saidha

(74) *Attorney, Agent, or Firm* — Armstrong Teasdale LLP

(57) ABSTRACT

The present invention relates to a process for treating an oil comprising a chlorophyll substrate, the process comprising contacting the oil with a polypeptide having decolorase activity or a composition comprising the polypeptide, wherein the polypeptide is selected from the group consisting of:

Figure 1:
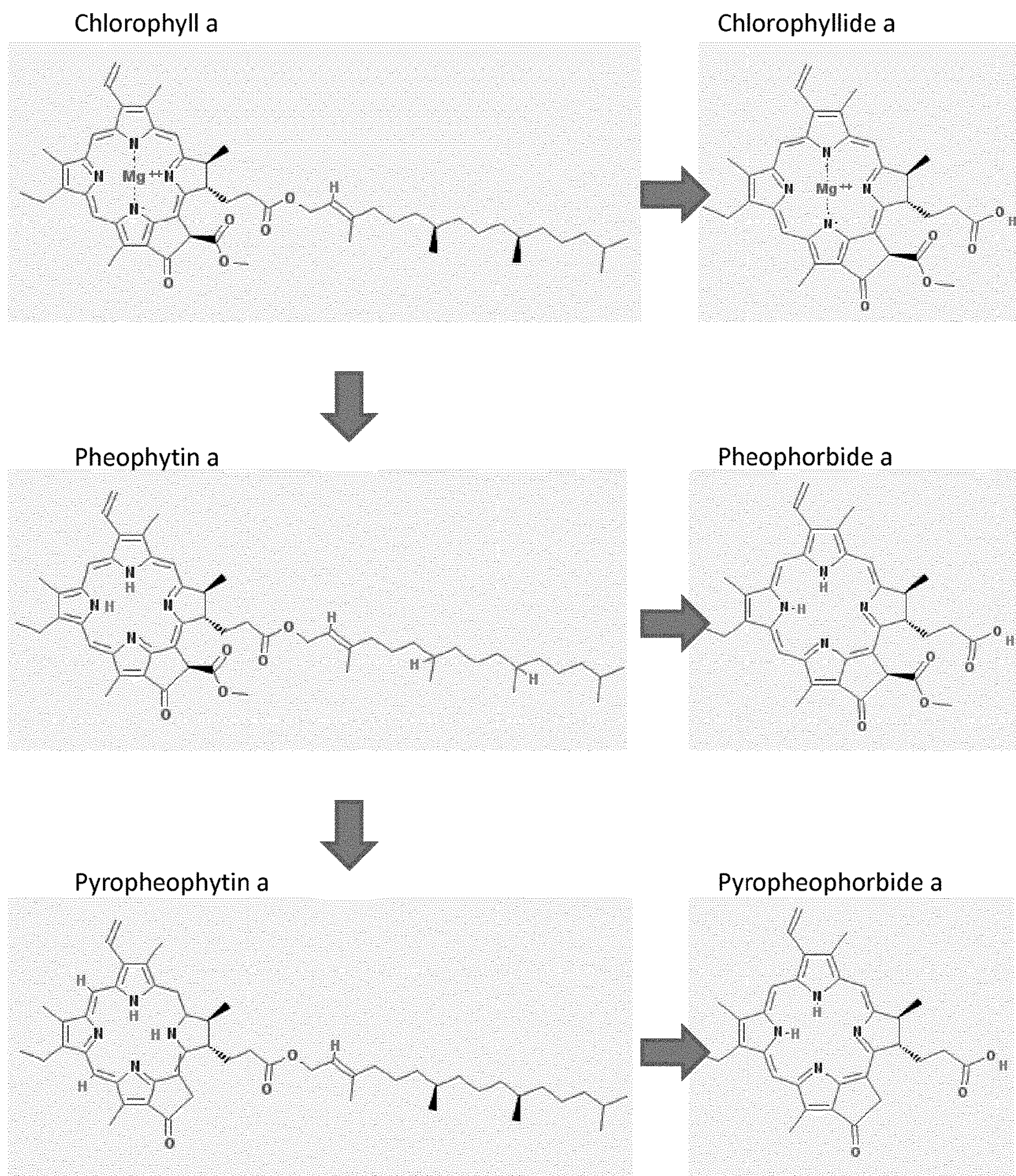

a. a polypeptide which has at least 80% identity to amino acids 1 to 318 of SEQ ID NO: 1; and, b. a polypeptide encoded by a nucleic acid sequence that has at least 80% identity to the nucleic acid sequence of SEQ ID NO: 2.

29 Claims, 15 Drawing Sheets

Specification includes a Sequence Listing.

Fig. 2

| | | pH 7 | | | | | | | | | |
|---|---|---|---|---|---|---|---|---|---|---|---|
| **Seq ID** | **Organism of origin** | **Sum phorbides** | **Sum phytines** | **Pheop horbide B** | **Pyro pheophorbid e B** | **Pheo phorbide A** | **Pyro pheophorbide A** | **Pheophyti n B** | **Pyro pheophyti n B** | **Pheo phytin A** | **Pyro pheophyt in A** |
| CHL25 | Gossypium raimondii | 275665 | 1931477 | 110063 | nd | 87548 | 78054 | 172154 | 480011 | 501490 | 777822 |
| CHL25 | Gossypium raimondii | 217243 | 1920403 | nd | nd | 146036 | 71207 | 150671 | 445076 | 499908 | 824748 |
| **CHL26** | **Hordeum vulgare _var._ distichum** | **1761172** | **nd** | **253499** | **344182** | **504095** | **659396** | **nd** | **nd** | **nd** | **nd** |
| **CHL26** | **Hordeum vulgar e_var._distic hum** | **544302** | **nd** | **57773** | **32433** | **211504** | **242592** | **nd** | **nd** | **nd** | **nd** |
| CHL27 | Phoenix dactylifera | 214854 | 2005118 | 93188 | nd | 54401 | 67265 | 166394 | 433895 | 561882 | 842947 |
| CHL27 | Phoenix dactylifera | 220930 | 2053900 | nd | nd | 117899 | 103031 | 193799 | 482559 | 555211 | 822331 |
| CHL28 | Wollemia_ nobilis | 136252 | 2098604 | nd | nd | 66640 | 69612 | 210029 | 501060 | 570068 | 817447 |
| CHL28 | Wollemia nobilis | 215865 | 1472498 | 67207 | 30122 | 51007 | 67529 | 167707 | nd | 529508 | 775283 |
| CHL29 | Cucumis sativus | 85466 | 2094838 | nd | nd | 47622 | 37844 | 197285 | 460480 | 572147 | 864926 |
| CHL29 | Cucumis sativus | 199316 | 1907160 | nd | 65112 | 59336 | 74868 | 219990 | 437255 | 425412 | 824503 |
| CHL30 | Tarenaya hassleriana | 407190 | 1651782 | 132167 | nd | 195116 | 79907 | 84617 | 459806 | 275750 | 831609 |
| CHL30 | Tarenaya hassleriana | 775787 | 1162942 | 147217 | 78822 | 370197 | 179551 | nd | 434141 | nd | 728801 |
| CHL31 | Solanum tuberosum | nd | 1946947 | nd | nd | nd | nd | 194042 | 519194 | 461284 | 772427 |
| CHL31 | Solanum tuberosum | 196969 | 2073336 | nd | nd | 88954 | 108015 | 218340 | 449385 | 587097 | 818514 |
| CHL32 | Populus trichocarpa | 125192 | 2010526 | nd | nd | 47822 | 77370 | 186712 | 469136 | 568785 | 785893 |
| CHL32 | Populus trichocarpa | 234302 | 1809325 | 67097 | 41140 | 60729 | 65336 | 145991 | 424868 | 500780 | 737686 |
| CHL33 | Vigna radiata | 206045 | 1981426 | nd | nd | 90029 | 116016 | 199490 | 443865 | 546929 | 791142 |

| | | | | | | | | | | | |
|---|---|---|---|---|---|---|---|---|---|---|---|
| CHL33 | Vigna radiata | 193761 | 2108416 | nd | nd | 87575 | 106186 | 217705 | 482949 | 580089 | 827673 |
| N1 | Negative control GFP | nd | 1974089 | nd | nd | nd | nd | 207234 | 469358 | 543483 | 754014 |
| N1 | Negative control GFP | nd | 2083472 | nd | nd | nd | nd | 248846 | 423746 | 596598 | 814282 |
| P2 | Postive control Chlamydomonas reinhardtii | 699847 | nd | nd | nd | 284290 | 415557 | nd | nd | nd | nd |
| P2 | Postive control Chlamydomonas reinhardtii | 738791 | nd | nd | nd | 313132 | 425659 | nd | nd | nd | nd |

Fig. 2 (continued)

Fig. 3

| | | pH 5 | | | | | | | | | |
|---|---|---|---|---|---|---|---|---|---|---|---|
| Poly-peptide | Organism of origin | sum phorbides | sum phytines | Pheophorbide B | Pyro-pheophorbide B | Pheophorbide A | Pyro-pheophorbide A | Pheophytin B | Pyro pheophytin B | Pheophytin A | Pyro pheophytin A |
| CHL25 | Gossypium raimondii | 682832 | 1665483 | 203729 | 123544 | 200295 | 155264 | 154662 | 415114 | 424929 | 670778 |
| CHL25 | Gossypium raimondii | 433068 | 1639813 | 141560 | 57416 | 135845 | 98247 | 126519 | 393480 | 419178 | 700636 |
| **CHL26** | **Hordeum vulgare _var. distichum** | **1961984** | **nd** | **288065** | **428220** | **515318** | **730381** | **nd** | **nd** | **nd** | **nd** |
| **CHL26** | **Hordeum vulgar e_var._distichum** | **1235980** | **nd** | **198696** | **271455** | **332811** | **433018** | **nd** | **nd** | **nd** | **nd** |
| CHL27 | Phoenix dactylifera | 206094 | 1798845 | nd | nd | 102826 | 103268 | 174535 | 405629 | 485365 | 733316 |
| CHL27 | Phoenix dactylifera | 280806 | 1733146 | 82107 | 32874 | 89643 | 76182 | 149358 | 439387 | 439352 | 705049 |
| CHL28 | Wollemia nobilis | 158680 | 2075438 | nd | nd | 69972 | 88708 | 238509 | 535100 | 531720 | 770109 |
| CHL28 | Wollemia nobilis | 191785 | 1914612 | nd | nd | 84514 | 107271 | 199692 | 485069 | 509453 | 720398 |
| CHL29 | Cucumis sativus | 395615 | 1979120 | 98132 | 52976 | 114957 | 129550 | 236918 | 464484 | 506263 | 771455 |
| CHL29 | Cucumis sativus | 124703 | 2016619 | nd | nd | 62823 | 61880 | 200440 | 520274 | 520436 | 775469 |
| CHL30 | Tarenaya hassleriana | 482799 | 1548865 | 131662 | nd | 245739 | 105398 | 85863 | 455875 | 270230 | 736897 |
| CHL30 | Tarenaya_hassleriana | 994370 | 1182489 | 266503 | 106789 | 442271 | 178807 | nd | 397455 | 120012 | 665022 |
| CHL31 | Solanum tuberosum | 184629 | 1725831 | 40036 | 36792 | 42879 | 64922 | 146351 | 439657 | 456005 | 683818 |
| CHL31 | Solanum tuberosum | 151987 | 1755184 | nd | nd | 70020 | 81967 | 174556 | 427006 | 476779 | 676843 |
| CHL32 | Populus trichocarpa | 197752 | 1764263 | 43990 | 38111 | 37199 | 78452 | 157704 | 428592 | 469300 | 708667 |
| CHL32 | Populus trichocarpa | 393823 | 2227493 | 67553 | nd | 133308 | 192962 | 255280 | 552761 | 602588 | 816864 |
| CHL33 | Vigna radiata | 182783 | 1854267 | nd | nd | 76870 | 105913 | 189671 | 461626 | 484065 | 718905 |
| CHL33 | Vigna radiata | 206810 | 2013555 | nd | nd | 91980 | 114830 | 234141 | 494192 | 526247 | 758975 |
| N1 | Negative control GFP | 146294 | 1831921 | nd | nd | 74351 | 71943 | 191888 | 404939 | 504627 | 730467 |
| N1 | Negative control GFP | 299942 | 1757280 | 79849 | 40073 | 93101 | 86919 | 172642 | 420907 | 468692 | 695039 |
| P2 | Postive control Chlamydomonas reinhardtii | 1141781 | nd | 132388 | 225164 | 302417 | 481812 | nd | nd | nd | nd |
| P2 | Postive control Chlamydomonas reinhardtii | 1175042 | nd | 138320 | 240386 | 314910 | 481426 | nd | nd | nd | nd |

Fig. 4 a)

| | a | | | | | b | | | | | |
|---|---|---|---|---|---|---|---|---|---|---|---|
| | CHYL | PYN | PPYN | POB | PPOB | CHYL | PYN | PPYN | POB | PPOB | Total |
| | ppm | | | ppm | | ppm | | | ppm | | ppm |
| Crude Canola | b.d. | 1.00 | 8.90 | b.d. | 0.50 | b.d. | 0.12 | 4.70 | b.d. | 0.18 | 15.40 |
| EDLC94 | b.d. | b.d. | 0.14 | 0.38 | 4.89 | b.d. | b.d. | 0.07 | 0.20 | 2.71 | 8.39 |
| CHL026 | b.d. | b.d. | 0.81 | 0.48 | 4.58 | b.d. | b.d. | 0.45 | 0.22 | 2.61 | 9.15 |

CHL=Chlorophyll; PYN= Pheophytin; PPYN= Pyropheophytin; POB= Pheophorbide; PPOB= Pyroppheophorbide
b.d. = below detection b)

| | PC | PE | PI | PA | lyso-PC | lyso-PE | lyso-PI | lyso-PA | C | E | I | A |
|---|---|---|---|---|---|---|---|---|---|---|---|---|
| | (%) | (%) | (%) | (%) | (%) | (%) | (%) | (%) | (%) | (%) | (%) | (%) |
| EDLC94 | 0.81 | 0.22 | 0.54 | 0.31 | 4.37 | 1.29 | 2.17 | 1.09 | 0.08 | b.d. | b.d. | 0.11 |
| CHL026 | 0.39 | 0.22 | 0.18 | 0.11 | 3.14 | 0.85 | 1.69 | 0.93 | 0.08 | 0.04 | b.d. | 0.14 |

PC = Phosphatidyl Choline; PE = Phosphatidyl Ethanolamine; PI = Phosphatidyl Inositol; PA = Phosphatidic Acid
C = phosphocholine; E = phosphoethanolamine; I = phosphoinositol; A = phosphate
b.d. = below detection

Fig. 5 a)

| | a | | | | | b | | | | | |
|---|---|---|---|---|---|---|---|---|---|---|---|
| | **CHYL** | **PYN** | **PPYN** | **POB** | **PPOB** | **CHYL** | **PYN** | **PPYN** | **POB** | **PPOB** | **Total** |
| | **ppm** | | | **ppm** | | **ppm** | | | **ppm** | | **ppm** |
| **Crude Canola Oil Start Material** | b.d. | 0.90 | 8.20 | b.d. | 0.63 | b.d. | 0.13 | 3.90 | b.d. | 0.27 | 14.03 |
| **Rxn 3 - CHL26** | b.d. | 0.15 | 2.60 | 0.69 | 4.65 | b.d. | 0.04 | 1.40 | 0.23 | 2.40 | 12.16 |
| **Rxn 4 - ELDC94** | b.d. | 0.23 | 6.70 | 0.60 | 1.30 | b.d. | 0.05 | 3.30 | 0.12 | 0.60 | 12.90 |
| **Rxn 5 - CHL26** | b.d. | 0.29 | 4.30 | 0.48 | 3.40 | b.d. | 0.06 | 2.20 | 0.11 | 1.70 | 12.54 |
| **Rxn 6 - CHL26** | b.d. | 0.26 | 3.80 | 0.64 | 3.70 | b.d. | 0.05 | 1.90 | 0.17 | 1.90 | 12.42 |
| **Rxn 7 - CHL26** | b.d. | b.d. | 0.82 | 0.79 | 5.90 | b.d. | b.d. | 0.44 | 0.13 | 3.20 | 11.28 |
| **Crude Soybean Oil** | 0.1 | 0.10 | 0.11 | b.d. | b.d. | b.d. | b.d. | b.d. | b.d. | b.d. | 0.31 |
| **Rxn 8 -CHL26** | b.d. | 0.11 | 0.12 | b.d. | b.d. | b.d. | b.d. | 0.05 | b.d. | b.d. | 0.28 |

CHYL=Chlorophyll; PYN= Pheophytin; PPYN= Pyropheophytin; POB= Pheophorbide; PPOB= Pyroppheophorbide
b.d.=below detection

Fig. 5 b)

| | PC | PE | PI | PA | lyso-PC | lyso-PE | lyso-PI | lyso-PA | C | E | I | A |
|---|---|---|---|---|---|---|---|---|---|---|---|---|
| | (%) | (%) | (%) | (%) | (%) | (%) | (%) | (%) | (%) | (%) | (%) | (%) |
| **Rxn 3 - CHL26 Gums** | b.d. | b.d. | b.d. | b.d. | 0.12 | 0.4 | 0.92 | 1.11 | 0.14 | b.d. | b.d. | b.d. |
| **Rxn 4 - ELDC94 Gums** | b.d. | b.d. | b.d. | b.d. | 0.35 | 0.6 | 1.12 | 1.14 | 0.13 | b.d. | b.d. | b.d. |
| **Rxn 5 - CHL26 Gums** | b.d. | b.d. | b.d. | 0.11 | 0.13 | 0.6 | 1.19 | 1.29 | 0.17 | b.d. | b.d. | b.d. |
| **Rxn 6 - CHL26 Gums** | b.d. | b.d. | b.d. | b.d. | b.d. | 0.6 | 1.06 | 1.08 | 0.13 | b.d. | b.d. | b.d. |
| **Rxn 7 - CHL26 Gums** | 0.44 | 0.57 | 0.42 | 0.41 | 3.81 | 3.11 | 0.87 | 0.94 | 0.05 | b.d. | b.d. | b.d. |
| **Rxn 8 - CHL26 SBO Gums** | b.d. | b.d. | b.d. | b.d. | 0.11 | 0.2 | 0.21 | 0.17 | 0.09 | 0.11 | 0.23 | 0.27 |

PC = Phosphatidyl Choline; PE = Phosphatidyl Ethanolamine; PI = Phosphatidyl Inositol; PA = Phosphatidic Acid
C = phosphocholine; E = phosphoethanolamine; I = phosphoinositol; A = phosphate
b.d. = below detection

Fig. 5 c)

| | a | | | | | b | | | | | |
|---|---|---|---|---|---|---|---|---|---|---|---|
| | CHYL | PYN | PPYN | POB | PPOB | CHYL | PYN | PPYN | POB | PPOB | Total |
| | ppm | | | ppm | | ppm | | | ppm | | ppm |
| **Rxn 3 - CHL26 Gums** | b.d. | b.d. | 0.06 | 0.59 | 4.30 | b.d. | b.d. | b.d. | b.d. | 1.50 | 6.45 |
| **Rxn 4 - ELDC94 Gums** | b.d. | b.d. | 0.11 | 0.50 | 2.00 | b.d. | b.d. | 0.07 | b.d. | 0.56 | 3.24 |
| **Rxn 5 - CHL26 Gums** | b.d. | b.d. | 0.16 | 0.20 | 1.80 | b.d. | b.d. | 0.14 | b.d. | 0.68 | 2.98 |
| **Rxn 6 - CHL26 Gums** | b.d. | b.d. | 0.13 | 0.14 | 1.30 | b.d. | b.d. | 0.06 | b.d. | 0.55 | 2.18 |
| **Rxn 7 - CHL26 Gums** | b.d. | b.d. | b.d. | 0.22 | 3.30 | b.d. | b.d. | b.d. | b.d. | 1.50 | 5.02 |
| **Rxn 8 - CHL26 SBO Gums** | b.d. | b.d. | b.d. | 0.44 | 0.12 | b.d. | b.d. | b.d. | b.d. | b.d. | 0.56 |

CHYL=Chlorophyll; PYN= Pheophytin; PPYN= Pyropheophytin; POB= Pheophorbide; PPOB= Pyroppheophorbide
b.d.= below detection;

SBO=Soybean oil

Fig. 6

| | a | | | | | a' | | b | | | | | b' | | | |
|---|---|---|---|---|---|---|---|---|---|---|---|---|---|---|---|---|
| | CHYL | PYN | PPYN | POB | PPOB | PYN | POB | CHYL | PYN | PPYN | POB | PPOB | CHYL | PYN | POB | Total |
| | ppm | | | ppm | | ppm | | ppm | | | ppm | | ppm | | ppm | ppm |
| **ORCAN** | 0.08 | 9.29 | 6.69 | b.d. | b.d. | 4.80 | b.d. | 0.17 | 2.23 | 2.83 | b.d. | b.d. | 0.11 | 1.20 | b.d. | 27.38 |
| Rxn 9 - ELDC94 | 0.17 | 1.96 | 3.01 | 2.65 | 1.06 | 1.50 | 0.30 | 0.12 | 0.66 | 0.81 | 0.07 | 0.20 | b.d. | 0.30 | 0.05 | 12.86 |
| Rxn 10 - ELDC94 | 0.08 | 4.77 | 6.22 | 0.22 | 0.14 | 3.19 | 0.06 | 0.11 | 1.28 | 2.82 | b.d. | b.d. | b.d. | 0.9 | b.d. | 19.79 |
| Combined 9 & 10 | 0.19 | 5.97 | 6.85 | 0.18 | 0.15 | 1.85 | 0.05 | 0.12 | 1.64 | 1.58 | b.d. | b.d. | b.d. | 0.50 | b.d. | 19.10 |
| Rxn 11 - CHL26 | 0.09 | 1.96 | 3.01 | 2.96 | 1.17 | 3.38 | 0.32 | 0.12 | 0.73 | 1.69 | 0.16 | 0.34 | b.d. | 0.62 | b.d. | 16.56 |
| Rxn 12 - CHL26 | n.m. | n.m. | n.m. | n.m. | n.m. | n.m. | n.m. | n.m. | n.m. | n.m. | n.m. | n.m. | n.m. | n.m. | n.m. | n.m. |
| Combined 11 & 12 | 0.10 | 2.22 | 3.18 | 3.03 | 1.29 | 3.16 | 0.28 | 0.12 | 0.73 | 1.73 | 0.86 | 0.64 | 0.12 | 0.64 | 0.08 | 18.19 |
| **ORSBO** | 0.21 | 0.70 | 0.24 | b.d. | ND | 1.26 | b.d. | 0.28 | 0.24 | 0.49 | b.d. | b.d. | b.d. | 0.43 | b.d. | 3.85 |
| Rxn 13 - ELDC94 | 0.17 | 0.31 | 0.05 | 0.03 | 0.03 | b.d. | b.d. | 0.22 | 0.11 | 0.23 | b.d. | b.d. | b.d. | b.d. | b.d. | 1.15 |
| **ORSBO** | 0.22 | 0.72 | 0.25 | b.d. | b.d. | 1.27 | b.d. | 0.26 | 0.24 | 0.52 | b.d. | b.d. | b.d. | 0.43 | b.d. | 3.90 |

| | a | | | | | a' | | b | | | | | b' | | | |
|---|---|---|---|---|---|---|---|---|---|---|---|---|---|---|---|---|
| | **CHYL** | **PYN** | **PPYN** | **POB** | **PPOB** | **PYN** | **POB** | **CHYL** | **PYN** | **PPYN** | **POB** | **PPOB** | **CHYL** | **PYN** | **POB** | **Total** |
| | **ppm** | | | **ppm** | | **ppm** | | **ppm** | | | **ppm** | | **ppm** | | **ppm** | **ppm** |
| Rxn 14 - CHL26 | 0.17 | 0.31 | 0.08 | 0.05 | 0.05 | b.d. | 0.03 | 0.22 | 0.11 | 0.23 | 0.03 | 0.05 | 0.11 | ND | b.d. | 1.41 |
| **Ref. SBO** | 0.20 | 0.71 | 0.26 | b.d. | b.d. | 1.27 | b.d. | 0.27 | 0.23 | 0.52 | b.d. | b.d. | b.d. | 0.43 | b.d. | 3.90 |
| Rxn 15 - ELDC94 | 0.17 | 0.33 | 0.13 | b.d. | b.d. | 0.62 | b.d. | 0.22 | 0.11 | 0.25 | b.d. | b.d. | b.d. | 0.21 | b.d. | 2.05 |
| **Ref SBO** | 0.21 | 0.36 | 0.12 | b.d. | b.d. | 0.63 | b.d. | 0.28 | 0.12 | 0.26 | b.d. | b.d. | b.d. | 0.21 | b.d. | 2.19 |
| Rxn 16 - CHL26 | 0.17 | 0.32 | 0.10 | 0.04 | 0.03 | 0.61 | b.d. | 0.22 | 0.11 | 0.24 | b.d. | b.d. | b.d. | b.d. | b.d. | 1.84 |

(Fig. 6 continued)

CHYL=Chlorophyll; PYN= Pheophytin; PPYN= Pyropheophytin; POB= Pheophorbide; PPOB= Pyroppheophorbide
b.d.= below detection; n.m. = not measured ORCAN=Once refined Canola oil; ORSBO= Once refined soybean oil; SBO=Soybean oil

SEQUENCE LISTING

```
Sequence total quantity: 14
SEQ ID NO: 1            moltype = AA  length = 318
FEATURE                 Location/Qualifiers
REGION                  1..318
                        note = CHL26 putative chlorophyllase
source                  1..318
                        mol_type = protein
                        organism = Hordeum vulgare
SEQUENCE: 1
MASAGDVFDH GRHGTSLARV EQAKNTRCSA ASRVDADAQA QQSPPKPLLV AAPCDAGEYP  60
VVVFLHGYLC NNYFYSQLIQ HVASHGFIVV CPQLYTVSGP DTTSEINSAA AVIDWLAAGL  120
SSKLAPGIRP NLAAVSISGH SRGGKVAFAL GLGHAKTSLP LAALIAVDPV DGTGMGNQTP  180
```

```
PPILAYKPNA IRVPAPVMVI GTGLGELPRN ALFPPCAPLG VSHAAFYDEC AAPACHLVAR  240
DYGHTDMMDD VTTGAKGLAT RALCKSGGAR APMRRFVAGA MVAFLNKWVE GKPEWLDAVR  300
EQTVAAPVVL SAVEFRDE                                                 318

SEQ ID NO: 2            moltype = DNA  length = 957
FEATURE                 Location/Qualifiers
misc_feature            1..957
                        note = Codon optimized nucleic acid sequence encoding a
                         putativechlorophyllase from Hordeum vulgare CHL26
source                  1..957
                        mol_type = other DNA
                        organism = synthetic construct
SEQUENCE: 2
atggcatcag caggggacgt atttgatcat ggacggcacg gaaccagttt ggcgagggta  60
gaacaagcga agaacacccg ctgtagcgca gcgtcccgcg tggatgcgga cgcccaggct  120
cagcagtcgc cgcccaaacc cctcctggtt gcagccccat gcgacgcagg cgaatacccg  180
gtggtcgtat tccttcacgg ctacttgtgc aacaattact tctactcgca gctgatccag  240
catgtcgcga gccacggctt cattgtagtg tgcccgcagc tgtataccgt gtctggtccg  300
gatacaacca gtgaaattaa tagcgccgct gccgtcatcg actggctcgc ggcaggactg  360
tcgtccaagc tggccccagg catccgtccg aacctggccg ccgtgagcat cagcggccac  420
tcacgcggtg gcaaggtggc ctttgccctg ggtctggggc atgccaagac cagcttgccg  480
ctggctgccc tgattgccgt ggatccagtc gacggcaccg ggatgggcaa ccaaactccc  540
cctccgatcc tggcctataa gccgaacgcc attcgggtcc ctgctcccgt gatggtgatc  600
ggcacaggac tgggcgaact gcctcgcaac gcgctgtttc caccttgcgc ccccttgggt  660
gtgtcgcacg ccgcgttcta cgatgagtgt gccgcacccg catgccacct ggttgcccgc  720
gactatggcc acaccgacat gatggatgac gtaacaaccg gcgccaaagg cctggcaacc  780
cgtgcgctgt gcaagagcgg tggggcaaga gccccgatgc gccgttttgt cgccggcgct  840
atggtggcgt tcctgaataa gtgggtggag ggcaagccgg aatggttgga cgccgtgcgc  900
gaacagaccg tggctgcacc ggtggtcctg tccgccgtag agtttcgcga tgagtaa     957

SEQ ID NO: 3            moltype = AA  length = 309
FEATURE                 Location/Qualifiers
REGION                  1..309
                        note = CHL25 putative chlorophyllase
source                  1..309
                        mol_type = protein
                        organism = Gossypium raimondii
SEQUENCE: 3
MSAPTSLATN VFGFGSYTTM LQKVESVTTS SMPVPPPKSL LIATPSEAGE FPLLIFLHGY  60
LLYNSFYSQL LQHVASHGFI VIAPQLYIVA GPDTTDEIKS TAAITNWLSK GVLQGLLPPY  120
VRPNLSKLAL AGHSRGGKVA FALALQKTMT KLKFSTLIGI DPVDGMDKGK QTPPPVLTYI  180
PHSFDLDMAV MVIGSGLGEV KRNPLFPPCA PKGVNHEDFF KECRKPACHI VAKDYGHLDM  240
LDDETNGFRG RSSYCLCKNG EAREPMRRFV GGVVVASMKA YLNGDNTDLI AIKGHEAAPV  300
ELKTIEFLV                                                           309

SEQ ID NO: 4            moltype = AA  length = 306
FEATURE                 Location/Qualifiers
REGION                  1..306
                        note = CHL27 putative chlorophyllase
source                  1..306
                        mol_type = protein
                        organism = Phoenix dactylifera
SEQUENCE: 4
MASVIINKPS ATAASVFDYG KLHVDTIPAK QSDESSPPKD ILVVCPKVAG SYTVVLFIQG  60
YLLSNAYYTQ LLQHVASHGF ILIAPQCIVV SPYSEEDITS AAAVTNWLSD GLQSVLPTGV  120
EANLDKLALA GHSRGGHAAF ALALGHAETT LKFSLLMGID PVAGPSKCCQ IPPKILTYEP  180
SSFELEIPVL VLGTGLGSEQ KNILFPACAP DGVNHKEFYS ECKPPCYHFV VTDYGHLDML  240
DDTAPKITKC VCKNGTNCRE IMRRTTGGIM TAFLKAYLLD LEEDLKAIAD PQIAPTKLDP  300
VSYRLE                                                              306

SEQ ID NO: 5            moltype = AA  length = 326
FEATURE                 Location/Qualifiers
REGION                  1..326
                        note = CHL28 putative chlorophyllase
source                  1..326
                        mol_type = protein
                        organism = Phoenix dactylifera
SEQUENCE: 5
MGLEDIFKEG PLPIQTLTIP AQQRATATGP CCHGRASPME PTALPPKPLM VILPSQEGDY  60
PVLLYLHGYL LLNSYYSQLL CHIASHGYIA IAPQMYTAAG PDATPEIRDA VAITEWLPTG  120
FAGRLPTHVR PDLQKVAVAG HSRGGKVAFG AALGRATPPP SLPYAAIVGV DPVDGMAAGR  180
QTPPLILGYG DHDFENSIPA LVIGSGLGPV RRNPLFPPCA PAGVNHVDFF RECRAPAYHF  240
VATEYGHQDF LDDETGGVRG RATYCLCKNG TAREPMRRFA AGIIVAFLNA WLRNDSADLE  300
DVLDPSRAPV KMEPPEWNLF QKVPTL                                        326

SEQ ID NO: 6            moltype = AA  length = 328
FEATURE                 Location/Qualifiers
REGION                  1..328
                        note = CHL29 putative chlorophyllase
```

```
source                  1..328
                        mol_type = protein
                        organism = Cucumis sativus
SEQUENCE: 6
MAAVVVDVKG KSKSAAVSSV VDLDPHPYDG VFEKGKFEVG VITKTTDIFS TSKPLLVFTP  60
KTPGLYPAIL FFHGFSCYGS FYTDFLTLIA SHGYVIAAPQ LYVMPTTSEM DEIKSAVDVI  120
KWLSSGLDPL LPTNVKGDLS KLSLLGHSRG GKTAFSLALG WGSPSLPFSA IIGIDPVAGS  180
KFFRPEPQIL DPPSQPFKIS LPITVVGTGL GPQKATPVTC ACAPDGLNHI AFFKKCKPTC  240
AHFVAVNYGH MDILDDNPPG MTGYFTNIAC KNGKGPRDLM RKCCSGLVVA SLKAYLDNDV  300
SILNAIYDPS IAPTELNPVE VIYKTPSA                                    328

SEQ ID NO: 7            moltype = AA  length = 317
FEATURE                 Location/Qualifiers
REGION                  1..317
                        note = CHL30 putative chlorophyllase
source                  1..317
                        mol_type = protein
                        organism = Tarenaya hassleriana
SEQUENCE: 7
MGEESERLGS SAFEPGSLPT TVIKADPSRE DPVSPPKPVM IVAPTVAGTY PVVFFFHGFY  60
LRNYFYSDVL SHVASHGFIL VAPQLCKLLP PGGQVEVDDA GKVINWAPKY LKSLLPGSVK  120
PSGEDTSLVG HSRGGKTAFA VALGHASTLD PSTKFSALVG IDPVAGSNVC MRTQPHILTY  180
EPESFELDMP VAVVGTGLGP KWNNVMPPCA PDGVNHKEFF NECRPTRAHF VAADYGHMDM  240
LDDDLEGAVG YLAGCLCKKG KLDKSGMRRF VGGIVVAFLK YSVFGDKSEI NSIVKDPSLS  300
PARIDPPPQF HEASSFV                                                317

SEQ ID NO: 8            moltype = AA  length = 306
FEATURE                 Location/Qualifiers
REGION                  1..306
                        note = CHL31 putative chlorophyllase
source                  1..306
                        mol_type = protein
                        organism = Solanum tuberosum
SEQUENCE: 8
MVHGKASIER NIKMGASSIF EIGNETINTI NVKSSSSLPC SLLVFSPTTK GSYPVLLFFH  60
GFMLQPSWYK SLLQHISSHR YIIVAPQFPL INLQEMKNVR KIAEWLINNL KSVVPEKVQP  120
DLEKVAISGH SKGGNTAFAV AFDSSMPLKF SALLGIEPVA GTSTSCLCPP YVLEYIPRIF  180
NQSIPVAVLG AGLSNQSTCC LLQSVAPNGV NHAEFFNESK PPCYYFMAKD YGHADMLEAE  240
GIMAILIRIL MKSGKGSKDS MIRAVGGIVV AFLKAYLEGQ IDDLNDIVKS PNLAPITLDP  300
VISIKD                                                            306

SEQ ID NO: 9            moltype = AA  length = 343
FEATURE                 Location/Qualifiers
REGION                  1..343
                        note = CHL32 putative chlorophyllase
source                  1..343
                        mol_type = protein
                        organism = Populus trichocarpa
SEQUENCE: 9
MAAIEDSPTF SSVVTPAAFE IGSLPTTEIP VDPVENDSTA PPGSLLIFRP EEKGTYPVIL  60
FHHGTGCQNS WYTDVFKFIS SHGYIVVAPQ LYGLMPPSGQ DELDLAAEVA NWLPSGLRCV  120
LPEDIEGDIH NLALAGHSRG GYIAFALALG LADVSLDVDF SALIGVDPVA GTSKTNQMEP  180
KILNYESCSF NFSIPVAIIG TGLGNKPACP IIRQTCAPDG VSHTEIFNEC KPPCSHFVTT  240
DYGHMDVLDD DIGLIGEGAR AMCKGSRRGV SRDPMRRTVG GVSVAFLEAF FKGNYTDYNK  300
ILKSNYFAPT TLDPVQNKSE GTSSSSLSAM SMPATLDWHI DEL                   343

SEQ ID NO: 10           moltype = AA  length = 318
FEATURE                 Location/Qualifiers
REGION                  1..318
                        note = CHL33 putative chlorophyllase
source                  1..318
                        mol_type = protein
                        organism = Vigna radiata
SEQUENCE: 10
MAAIEDSPTF SSVVTPAAFE IGSLPTTEIP VDPVENDSTA PPKPLLIFTP TVPGAYPVIL  60
FCHGFFVPNT FYSHLLTHIV SHGFILVAPQ LFCKGLPMLE PSEVKFAGKV ADWLAEGLQP  120
LLPENVEANL EKLVVSGHSK GGKTAFCVAL GYAKTKLKFS ALVGIDPVAG TSKYCETNPH  180
ILKGVPGSFN LNMPVAVIGS ELGPKKGNCC SPPCAPDGMN HKEFFKECKP PSAHFVVARY  240
GHMDMLDDET AGVIGTLLSK CACKNGSGPR DLMRRTIGGL VVAFLRAQLN DHWKDFDAIL  300
NPNIAPTQLD NMVYIPAS                                               318

SEQ ID NO: 11           moltype = AA  length = 236
FEATURE                 Location/Qualifiers
REGION                  1..236
                        note = Green fluorescent protein
source                  1..236
                        mol_type = protein
                        organism = synthetic construct
SEQUENCE: 11
```

-continued

```
MTALTEGAKL FEKEIPYITE LEGDVEGMKF IIKGEGTGDA TTGTIKAKYI CTTGDLPVPW  60
ATLVSTLSYG VQCFAKYPSH IKDFFKSAMP EGYTQERTIS FEGDGVYKTR AMVTYERGSI  120
YNRVTLTGEN FKKDGHILRK NVAFQCPPSI LYILPDTVNN GIRVEFNQAY DIEGVTEKLV  180
TKCSQMNRPL AGSAAVHIPR YHHITYHTKL SKDRDERRDH MCLVEVVKAV DLDTYQ      236

SEQ ID NO: 12          moltype = AA  length = 301
FEATURE                Location/Qualifiers
REGION                 1..301
                       note = P2 pyropheophytinase
source                 1..301
                       mol_type = protein
                       organism = Chlamydomonas reinhardtii
SEQUENCE: 12
MSDDYIKRGD LPTSKWSGRV TLRVDSAMAV PLDVVITYPS SGAAAYPVLV MYNGFQAKAP  60
WYRGIVDHVS SWGYTVVQYT NGGLFPIVVD RVELTYLEPL LTWLETQSAD AKSPLYGRAD  120
VSRLGTMGHS RGGKLAALQF AGRTDVSGCV LFDPVDGSPM TPESADYPSA TKALAAAGRS  180
AGLVGAAITG SCNPVGQNYP KFWGALAPGS WQMVLSQAGH MQFARTGNPF LDWSLDRLCG  240
RGTMMSSDVI TYSAAFTVAW FEGIFRPAQS QMGISNFKTW ANTQVAARSI TFDIKPMQSP  300
Q                                                                 301

SEQ ID NO: 13          moltype = DNA  length = 21
FEATURE                Location/Qualifiers
misc_feature           1..21
                       note = SpeI site and ribosome binding site
source                 1..21
                       mol_type = other DNA
                       organism = synthetic construct
SEQUENCE: 13
actagtagga ggtaactaat g                                           21

SEQ ID NO: 14          moltype = DNA  length = 12
FEATURE                Location/Qualifiers
misc_feature           1..12
                       note = stop codon and XhoI site
source                 1..12
                       mol_type = other DNA
                       organism = synthetic construct
SEQUENCE: 14
tgatgactcg ag                                                     12
```

ENZYMATIC REMOVAL OF CHLOROPHYLL SUBSTRATES FROM TRIACYLGLYCEROL-BASED OILS

CROSS-REFERENCE TO RELATED APPLICATIONS

This application is a continuation of U.S. patent application Ser. No. 16/650,599, filed Mar. 25, 2020, which is the 35 U.S.C. § 371 U.S. National Phase of International Patent Application No. PCT/EP2018/076130, filed Sep. 26, 2018, which claims the benefit of U.S. Provisional Patent Application Nos. 62/736,126, filed Sep. 25, 2018, and 62/736,129, filed Sep. 25, 2018, and claims priority to European Patent Application No. 17193211.4, filed Sep. 26, 2017, the disclosures of which are incorporated herein by reference in their entirety.

FIELD

The present invention relates to a novel polypeptide having decolorase activity, and a process for treating an oil comprising chlorophyll substrates.

SEQUENCE LISTING

The instant application contains a Sequence Listing which has been submitted electronically in ASCII format and is hereby incorporated by reference in its entirety. Said ASCII copy, created on Aug. 8, 2022 is named SEQ_LIST-54947923.XML and is 22,813 bytes in size.

BACKGROUND

Crude triacylglycerol oils obtained from either pressing or solvent extraction methods are a complex mixture of triacylglycerols, phospholipids, sterols, tocopherols, diacylglycerols, free fatty acids, trace metals, chlorophylls, beta-carotene, and other minor compounds. It is desirable to remove the phospholipids, free fatty acids, trace metals, chlorophylls, and beta-carotene in order to produce a quality fully refined oil or a salad oil with a bland taste, light color, and a long shelf life.

The removal of phospholipids generates the largest amount of neutral oil losses associated with the refining of triacylglycerol oils. The removal of chlorophylls generates the second largest amount of neutral oil losses associated with the refining of triacylglycerol-based oils.

Several different techniques may be used for phospholipid removal, including water degumming, enzyme assisted water degumming, acid degumming, caustic refining, and enzymatic treatment.

Water degumming is usually applied to crude oils containing a high amount of hydratable phospholipids. Due to its mild characteristics, the phospholipids obtained can be used as lecithin (a natural emulsifier). The oil obtained from this technique is generally referred to in the industry as being "degummed," despite being only partially degummed. Since water degummed oil still contains high amounts of phospholipids, especially non-hydratable phospholipids, the use of other process techniques, such as caustic refining or phospholipase A (PLA) enzyme degumming, can be required to produce a finished, high quality oil having high stability and low color.

In the water degumming process, water is added to crude oil with mixing to aid the hydration of the phospholipids present in the oil. The hydration of the phospholipids or "gums" causes the gums to swell and agglomerate as a flocculent, which is subsequently separated from the remainder of the oil. The oil loss from water degumming processes may be significant, with a negative impact in the overall economic balance on the refined oil process cost.

Enzyme assisted water degumming is usually applied to crude oils containing a high amount of hydratable phospholipids, where the goal is to react all of the hydratable phospholipids and convert them into diacylglycerols increasing the oil yield, while maintaining the non-hydratable phospholipids in the oil. Enzymes utilized for this process are Phospholipase C (PLC) and Phosphatidyl Inositol Phospholipase (PI-PLC).

In the enzyme assisted water degumming process, water and PLCs are added to crude oil with mixing. The enzymes are then allowed to react with the phospholipids in the oil with shear mixing to aid in the conversion of phosphatidyl choline (PC), phosphatidyl ethanolamine (PE), and PI to diacylglycerols in the oil. The heavy phase (water, denature protein, and phosphor-compounds) has a specific gravity higher than that of the oil and may be separated by settling, filtration, or the industrial practice of centrifugation. The enzyme assisted water degumming process removes predominately only the hydratable phospholipids. The remaining phospholipids, measured as the salts of phosphatidic acid can be removed in subsequent processing operations.

Acid degumming is usually applied to crude oils when the goal is the total removal of phospholipids. The oil obtained is usually called "super-degummed" or "totally degummed" in the industry. Crude oil is treated with phosphoric acid or citric acid. The acid improves the hydrophilic nature of the non-hydratable phospholipids (NHPs), thus aiding in their removal. Water is then added to the acid-treated crude oil, and the oil is mixed to aid the hydration of the phospholipids. The hydration of the phospholipids or "gums" causes the gums to swell and agglomerate as a flocculent, which is subsequently removed. The acid degumming process removes most of the phospholipids, but enough still remain in the degummed oil to require additional processing. As in the water degumming process, some of the oil is emulsified, and is considered a process loss, with the negative economic impact on the overall economic balance of the refined oil process cost.

Caustic refining is usually applied to crude or water degummed oils when the goal is to remove all of the phospholipids and free fatty acids. Crude or water degummed oil is treated with phosphoric acid or citric acid. The acid improves the hydrophilic nature of the NHPs, thus aiding in their removal. A diluted sodium hydroxide solution is added to the acid-treated oil. The caustic solution neutralizes the free fatty acids (producing sodium soaps), neutralizes the excess acid, and with the sodium soaps created, assists in hydrating and emulsifying all the remaining phospholipids. The sodium hydroxide solution/oil is mixed and then separated by settling, filtration, or industrially by centrifugation. The caustic treated oil is then "washed" and centrifuged again. The oil from the centrifuge is known as "Once Refined" and the water is commonly known as "Wash Water". For food applications, the "once refined" oil is usually submitted for bleaching and deodorization to produce salad oil. An alternative to water washing is to treat the caustic treated oil with an absorbent silica gel and filter out the residual soaps and phospholipids not removed in the initial centrifugation.

"Enzymatic refining" or "enzymatic degumming" is used when the goal is the total removal of phospholipids. Generally, enzymatic degumming treatments of the prior art have been practiced on oils that have been degummed previously by one of the other methods, typically water degumming. For food applications, the enzyme degummed oil is sequentially submitted to bleaching and deodorization, a process known in the industry as "physical refining." Enzymatic degumming provides a better oil yield than water, acid, or caustic degumming, with improved economic results.

The enzymatic reaction changes the nature of the phospholipid, cleaving some of the phospholipid parts. This reduces the phospholipids' emulsification properties, so that less oil is lost when the gums are separated from the oil, thus saving oil. Enzymes exhibiting activity with phospholipids are commonly called "phospholipases". The types of phospholipase are based on the position on the phospholipid molecule at which the enzyme reacts, and are known as PLA1, PLA2, PLC, and PLD. Different types of phospholipases will yield different compounds upon reacting with the phospholipids.

Commercial PLA1 enzymes with phospholipase activity are Lecitase® Ultra and QuaraLowP. Commercial PLA2 enzymes with phospholipase activity are Rohalase Xtra and LysoMax. These products are known to yield polar lysophospholipids and polar fatty acids when mixed with degummed oil with a 1-1.5% water citric acid-NaOH buffer at 4.5<pH<7.0 and 40° C.<T<55° C. The PLA1 selectively hydrolyzes the fatty acid opposite the phosphate functional group on the glycerol backbone and the PLA2 selectively hydrolyzes the fatty acid in the center of the glycerol backbone of the phospholipid. PLAs are non-selective for the phospholipids they react with.

The resulting reaction yields a lyso-phospholipid and a fatty acid. The lyso-phospholipid molecule has lost one hydrophilic functional group, and the remaining alcohol group at the reaction site is hydrophilic. Now with two hydrophilic sites, the lyso-phospholipid molecule is water soluble, and has lost its emulsification properties. The PLA1 or PLA2 degumming process thus reduces refining losses by no longer removing any neutral oil with the gums, and the only loss is the original phospholipid molecule.

It is known in the art that PLC enzymes react with a phospholipid by selectively hydrolyzing the phosphate functional group. The resulting reaction yields a diacylglycerol ("DAG") and a phosphatidic group. The diacylglycerol molecule no longer has the phosphate functional group and does not need to be removed. The PLC degumming process reduces the refining loss by retaining the original phospholipid molecule, while removing only the phosphate functional group. However, PLC does not react with all of the phospholipids present in the oil. Generally, PLC does not react with either phosphatidic acid (PA) or phosphatidyl inositol (PI). A PI-PLC used in combination with PLC enables the reaction and removal of PC, PE, and PI. Yet the non-hydratable phosphatides that remain in oil after water degumming. Thus, the enzymatic assisted water degumming treated oil must be further treated with caustic to remove the residual gums.

Triacylglycerol oils from oilseeds such as soybean and canola, and oil fruits, such as palm and algal source oils, contain chlorophyll. Chlorophyll is removed during many stages of the oil production process, including seed crushing, oil extraction, degumming, caustic treatment and bleaching steps. In the last of these, the bleaching process residual chlorophyll is removed to achieve acceptable levels. This chlorophyll is typically removed from the oil in a bleaching process step involving heating the oil and running it through an adsorbent to remove chlorophyll and other color-bearing compounds that impact the appearance and/or stability of the finished oil.

High level of chlorophyll pigments imparts undesirable color and induce oxidation of oil during storage leading to a deterioration of the oil. In the edible oil processing industry, a bleaching step is employed to lower chlorophyll levels to as low as 0.02 ppm to guarantee oil quality in terms of color and organolepticity. This bleaching step increases processing cost and reduces oil yield due to entrainment in the bleaching clay. The "spent" clay then must be disposed of environmentally and is a hazardous material to transport due to the spontaneous combustion nature acid treated material and adsorbed oil, approximately 30% wt.

Chlorophyll is modified during oil processing into a derivative known as pheophytin, by the loss of the magnesium ion from the porphyrin (chlorine) ring (see FIG. 1). Typically, pheophytin is more abundant in oil during processing than chlorophyll. Pheophytin can be further degraded into pyropheophytin (see Behavior of Chlorophyll Derivatives in Canola Oil Processing", JAOCS, Vol. no. 9 Sep. 1993, p. 837-841). Pyropheophytin is predominantly formed processing of vegetable oils (see e.g. 'The lipid handbook' ed. Frank D. Gunstone, John L. Harwood, Albert J. Dijkstra. 2007—3rd ed., p. 56). Chlorophyll, pheophytin and pyropheophytin occur in two forms the A and B form. The A component has a methyl group at the C7 position. The B component has an aldehyde at the C7 position.

The use of enzymes for the removal of pyropheophytin in vegetable oils is known from WO2010/143149 and WO2013/160372. WO2010/143149 discloses methods for treating pyropheophytin-containing compositions using enzymes capable of hydrolysing pyropheophytin derived for instance from *Triticum aestivum* and *Chlamydomonas reinhardtii*. WO2013/160372 discloses several chlorophyllase enzymes for instance from *Arabidopsis thaliana* and *Triticum aestivum*, which were able to convert pheophytin and pyropheophytin in oil.

There is a need for alternative enzymes that are capable of hydrolysing chlorophyll substrates, such as pyropheophytin, and methods for the enzymatic hydrolysis of chlorophyll substrates, such as pyropheophytin.

SUMMARY

The present invention relates to a polypeptide having pyropheophytinase activity, which is selected from the group consisting of:

a. an isolated polypeptide which has at least 80%, 85%, 86%, 87%, 88%, 89%, 90%, 91%, 92%, 93%, 94%, 95%, 96%, 97%, 98% or at least 99%, or 100% identity to amino acids 1 to 318 of SEQ ID NO: 1; and,
b. a polypeptide encoded by a nucleic acid sequence that has at least 80%, 85%, 86%, 87%, 88%, 89%, 90%, 91%, 92%, 93%, 94%, 95%, 96%, 97%, 98% or at least 99%, or 100% identity to the nucleic acid sequence of SEQ ID NO: 2.

The invention further relates to a nucleic acid, which is selected from the group consisting of:

a. a nucleic acid sequence encoding a polypeptide as disclosed herein;
b. a nucleic acid which has at least 80%, 85%, 86%, 87%, 88%, 89%, 90%, 91%, 92%, 93%, 94%, 95%, 96%, 97%, 98% or at least 99% or 100% identity to SEQ ID NO: 2; and,
c. a nucleic acid according to a) or b) further comprising a promotor sequence and/or other control sequence.

The present disclosure also relates to a vector comprising a nucleic acid encoding a polypeptide as disclosed herein wherein the nucleic acid is operably linked to one or more control sequence(s) that direct expression of the polypeptide in a host cell.

Also disclosed is a recombinant host cell comprising a nucleic acid encoding a polypeptide as disclosed herein, or a vector as disclosed herein, wherein the nucleic acid is heterologous to the host cell.

In one aspect, the present disclosure relates to a method for producing a polypeptide as disclosed herein, comprising cultivating a host cell comprising a nucleic acid encoding a polypeptide as disclosed herein in a suitable fermentation medium under conditions that allow expression of the polypeptide and producing the polypeptide.

In one aspect, the present disclosure is directed to a process for treating an oil comprising a chlorophyll substrate, the process comprising contacting the oil with a polypeptide having decolorase activity or a composition comprising the polypeptide, wherein the polypeptide is selected from the group consisting of:

a. a polypeptide which has at least 80%, 85%, 86%, 87%, 88%, 89%, 90%, 91%, 92%, 93%, 94%, 95%, 96%, 97%, 98% or at least 99%, or 100% identity to amino acids 1 to 318 of SEQ ID NO: 1; and, b. a polypeptide encoded by a nucleic acid sequence that has at least 80%, 85%, 86%, 87%, 88%, 89%, 90%, 91%, 92%, 93%, 94%, 95%, 96%, 97%, 98% or at least 99%, or 100% identity to the nucleic acid sequence of SEQ ID NO: 2.

In one embodiment, a chlorophyll substrate is converted into a chlorophyll product. A chlorophyll substrate may be selected from the group consisting of chlorophyll, pheophytin, pyropheophytin, and combinations thereof, and the chlorophyll product may be selected from the group consisting of chlorophyllide, pheophorbide, pyropheophorbide, and combinations thereof.

In one aspect, the present disclosure relates to a process for treating an oil comprising pyropheophytin, the process comprising contacting the oil with a polypeptide having pyropheophytinase activity as disclosed herein, or a composition comprising a polypeptide as disclosed herein, wherein the pyropheophytin is converted into pyropheophorbide.

In another aspect, the present disclosure is directed to a process for treating an oil comprising a chlorophyll substrate, the process comprising contacting the oil with a polypeptide having decolorase activity or a composition comprising the polypeptide, wherein the treatment reduces the total concentration of chlorophyll substrates in the oil by at least 5% by weight, compared to the total concentration of chlorophyll substrates in the oil prior to treatment.

In another aspect, the disclosure is directed to a process for treating an oil comprising a chlorophyll substrate, the process comprising contacting the oil with a polypeptide having decolorase activity or a composition comprising the polypeptide, water, and optionally an additional enzyme, at a pH of from 4 to 8; stirring the resulting oil for from 0.5 to 24 hours; and adding a PLA enzyme to the oil following stirring. In one embodiment, the PLA enzyme is a PLA1 enzyme.

In another aspect, the present disclosure is directed to an oil produced by a process disclosed herein.

Definitions

The term "control sequence" can be used interchangeably with the term "expression-regulating nucleic acid sequence". The term as used herein refers to nucleic acid sequences necessary for and/or affecting the expression of an operably linked coding sequence in a particular host organism, or in vitro. When two nucleic acid sequences are operably linked, they usually will be in the same orientation and also in the same reading frame. They usually will be essentially contiguous, although this may not be required. The expression-regulating nucleic acid sequences, such as inter alia appropriate transcription initiation, termination, promoter, leader, signal peptide, propeptide, prepropeptide, or enhancer sequences; Shine-Dalgarno sequence, repressor or activator sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion, can be any nucleic acid sequence showing activity in the host organism of choice and can be derived from genes encoding proteins, which are either endogenous or heterologous to a host cell. Each control sequence may be native or foreign (heterologous) to the nucleic acid sequence encoding the polypeptide. When desired, the control sequence may be provided with linkers for the purpose of introducing specific restriction sites facilitating ligation of the control sequences with the coding region of the nucleic acid sequence encoding a polypeptide. Control sequences may be optimized to their specific purpose.

Chlorophyll derivatives as used herein include chlorophyll substrates and chlorophyll products. Chlorophyll substrates comprise chlorophyll, pheophytin and pyropheophytin. Chlorophyll products comprise chlorophyllide, pheophorbide and pyropheophorbide. Chlorophyll derivatives comprise so-called a and b compounds.

The term "decolorase" (as well as variations thereof, including the phrase "a polypeptide having decolorase activity"), as used herein, means the polypeptide is capable of converting one or more chlorophyll substrate into a chlorophyll product. For instance, the polypeptide may be capable of hydrolyzing chlorophyll into chlorophyllide; hydrolyzing pheophytin into pheophorbide; and/or hydrolyzing pyropheophytin into pyropheophorbide. The term "decolorase activity" thus may include chlorophyllase activity, pheophytinase activity, pyropheophytinase activity, or combinations thereof.

The term "triacylglycerol-based oil" refers to an oil comprising triacylglycerol.

The term "expression" includes any step involved in the production of the polypeptide including, but not limited to, transcription, post transcriptional modification, translation, post-translational modification, and secretion.

An expression vector comprises a polynucleotide coding for a polypeptide, operably linked to the appropriate control sequences (such as a promoter, RBS/Shine Delgado and transcriptional and translational stop signals) for transcription and/or translation in vitro, or in the host cell, of the polynucleotide.

The expression vector may be any vector (e.g., a plasmid or virus), which can be conveniently subjected to recombinant DNA procedures and can bring about the expression of the polynucleotide. The choice of the vector will typically depend on the compatibility of the vector with the cell into which the vector is to be introduced. The vectors may be linear or closed circular plasmids. The vector may be an autonomously replicating vector, i.e. a vector, which exists as an extra-chromosomal entity, the replication of which is independent of chromosomal replication, e.g., a plasmid, an extra-chromosomal element, a mini-chromosome, or an artificial chromosome. Alternatively, the vector may be one which, when introduced into the host cell, is integrated into the genome and replicated together with the chromosome(s) into which it has been integrated. The integrative cloning vector may integrate at random or at a predetermined target locus in the chromosomes of the host cell. The vector system may be a single vector or plasmid or two or more vectors or plasmids, which together contain the total DNA to be introduced into the genome of the host cell, or a transposon.

A host cell as defined herein is an organism suitable for genetic manipulation and one which may be cultured at cell densities useful for industrial production of a target product, such as a polypeptide according to the present invention. A host cell may be a host cell found in nature or a host cell derived from a parent host cell after genetic manipulation or classical mutagenesis. Advantageously, a host cell is a recombinant host cell.

A host cell may be a prokaryotic, archaebacterial, or eukaryotic host cell. A prokaryotic host cell may be, but is not limited to, a bacterial host cell. A eukaryotic host cell may be, but is not limited to, a yeast, a fungus, an amoeba, an alga, a plant, an animal, or an insect host cell.

The term "heterologous" as used herein refers to nucleic acid or amino acid sequences not naturally occurring in a host cell. In other words, the nucleic acid or amino acid sequence is not identical to that naturally found in the host cell.

A nucleic acid or polynucleotide sequence is defined herein as a nucleotide polymer comprising at least 5 nucleotide or nucleic acid units. A nucleotide or nucleic acid refers to RNA and DNA. The terms "nucleic acid" and "polynucleotide sequence" are used interchangeably herein.

A "peptide" refers to a short chain of amino acid residues linked by a peptide (amide) bonds. The shortest peptide, a dipeptide, consists of 2 amino acids joined by single peptide bond.

The term "polypeptide" refers to a molecule comprising amino acid residues linked by peptide bonds and containing more than five amino acid residues. The term "protein" as used herein is synonymous with the term "polypeptide" and may also refer to two or more polypeptides. Thus, the terms "protein" and "polypeptide" can be used interchangeably. Polypeptides may optionally be modified (e.g., glycosylated, phosphorylated, acylated, farnesylated, prenylated, sulfonated, and the like) to add functionality. Polypeptides exhibiting activity in the presence of a specific substrate under certain conditions may be referred to as enzymes. It will be understood that, as a result of the degeneracy of the genetic code, a multitude of nucleotide sequences encoding a given polypeptide may be produced.

An "isolated nucleic acid fragment" is a nucleic acid fragment that is not naturally occurring as a fragment and would not be found in the natural state.

The term "isolated polypeptide" as used herein means a polypeptide that is removed from at least one component, e.g. other polypeptide material, with which it is naturally associated. The isolated polypeptide may be free of any other impurities. The isolated polypeptide may be at least 50% pure, e.g., at least 60% pure, at least 70% pure, at least 75% pure, at least 80% pure, at least 85% pure, at least 80% pure, at least 90% pure, or at least 95% pure, 96%, 97%, 98%, 99%, 99.5%, 99.9% as determined by SDS-PAGE or any other analytical method suitable for this purpose and known to the person skilled in the art. An isolated polypeptide may be produced by a recombinant host cell.

The term "promoter" is defined herein as a DNA sequence that binds RNA polymerase and directs the polymerase to the correct downstream transcriptional start site of a nucleic acid sequence to initiate transcription. A promotor sequence may be native of or heterologous relative to the nucleic acid sequence encoding the polypeptide.

The term "recombinant" when used in reference to a cell, nucleic acid, protein or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all. The term "recombinant" is synonymous with "genetically modified" and "transgenic".

The terms "sequence identity" and "sequence homology" are used interchangeable herein. For the purpose of this invention, it is defined here that in order to determine the percentage of sequence homology or sequence identity of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/bases or amino acids. The sequence identity is the percentage of identical matches between the two sequences over the reported aligned region. The percent sequence identity between two amino acid sequences or between two nucleotide sequences may be determined using the Needleman and Wunsch algorithm for the alignment of two sequences. (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp. 276-277, http://emboss.bioinformatics.nl/). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the invention is calculated as follows: Number of corresponding positions in the alignment showing an identical amino acid or identical nucleotide in both sequences divided by the total length of the alignment after subtraction of the total number of gaps in the alignment. The identity as defined herein can be obtained from NEEDLE by using the NOBRIEF option and is labeled in the output of the program as "longest-identity".

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, word length=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and NBLAST) can be used. See the homepage of the National Center for Biotechnology Information at http://www.ncbi.nlm.nih.gov/.

A "synthetic molecule", such as a synthetic nucleic acid or a synthetic polypeptide is produced by in vitro chemical or enzymatic synthesis. It includes, but is not limited to, variant nucleic acids made with optimal codon usage for host organisms of choice.

A synthetic nucleic acid may be optimized for codon use, preferably according to the methods described in WO2006/077258 and/or WO2008000632, which are herein incorporated by reference. WO2008/000632 addresses codon-pair optimization. Codon-pair optimization is a method wherein the nucleotide sequences encoding a polypeptide that have been modified with respect to their codon-usage, in particular the codon-pairs that are used, are optimized to obtain improved expression of the nucleotide sequence encoding the polypeptide and/or improved production of the encoded polypeptide. Codon pairs are defined as a set of two subsequent triplets (codons) in a coding sequence. Those skilled in the art will know that the codon usage needs to be adapted depending on the host species, possibly resulting in variants with significant homology deviation from SEQ ID NO: 1, but still encoding the polypeptide according to the invention.

As used herein, the terms "variant", "derivative", "mutant" or "homologue" can be used interchangeably. They can refer to either polypeptides or nucleic acids. Variants include substitutions, insertions, deletions, truncations, transversions, and/or inversions, at one or more locations relative to a reference sequence. Variants can be made for example by site-saturation mutagenesis, scanning mutagenesis, insertional mutagenesis, random mutagenesis, site-directed mutagenesis, and directed-evolution, as well as various other recombination approaches known to a skilled person in the art. Variant genes of nucleic acids may be synthesized artificially by known techniques in the art.

DETAILED DESCRIPTION

Disclosed herein is a polypeptide having pyropheophytinase activity, which is selected from the group consisting of:

a. an isolated polypeptide which has at least 80%, 85%, 86%, 87%, 88%, 89%, 90%, 91%, 92%, 93%, 94%, 95%, 96%, 97%, 98% or at least 99%, or which has 100% identity to amino acids 1 to 318 of SEQ ID NO: 1; and, b. a polypeptide encoded by a nucleic acid sequence that has at least 80%, 85%, 86%, 87%, 88%, 89%, 90%, 91%, 92%, 93%, 94%, 95%, 96%, 97%, 98%, or 99%, or which has 100% identity to the nucleic acid sequence of SEQ ID NO: 2.

A polypeptide having pyropheophytinase activity may be a polypeptide which has at least 80% identity to amino acids 1 to 318 of SEQ ID NO: 1. A polypeptide as disclosed herein may have at least 85%, 86%, 87%, 88%, 89%, 90%, 91%, 92%, 93%, 94%, 95%, 96%, 97%, 98% or at least 99% identity to amino acids 1 to 318 of SEQ ID NO: 1. A polypeptide as disclosed herein may have at least 85%, 86%, 87%, 88%, 89%, 90%, 91%, 92%, 93%, 94%, 95%, 96%, 97%, 98%, or at least 99% identity to amino acids 1 to 318 of SEQ ID NO: 1. A polypeptide having pyropheophytinase activity as disclosed herein may comprise, or contain, or consist of amino acids 1 to 318 of SEQ ID NO: 1. A polypeptide having pyropheophytinase activity may comprise, or contain, or consist of amino acids 2 to 318 of SEQ ID NO: 1. Surprisingly, it was found that a polypeptide which has at least 80% identity to amino acids 1 to 318, or to amino acids 2 to 318 of SEQ ID NO: 1 comprises pyropheophytinase activity.

A polypeptide having pyropheophytinase activity hydrolyses pyropheophytin into pyropheophorbide (see also FIG. 1). A polypeptide having pyropheophytinase activity as disclosed herein preferably hydrolyses pyropheophytin a and pyropheophytin b into their pyropheophorbide a and b compounds. Accordingly, pyropheophytinase activity can be determined by the formation of pyropheophorbide.

A polypeptide as disclosed herein may further comprise pheophytinase activity. A polypeptide having pheophytinase activity hydrolyses pheophytin into pheophorbide. Preferably a polypeptide as disclosed herein hydrolyses pheophytin a and/or pheophytin b into their respective pheophorbide compounds. Accordingly, pheophytinase activity can be determined by the formation of pheophorbide.

A polypeptide as disclosed herein having pyropheophytinase activity may also comprise chlorophyllase activity. A polypeptide having chlorophyllase activity hydrolyses the conversion of chlorophyll into chlorophyllide. Preferably a polypeptide as disclosed herein hydrolyses chlorophyll a and/or chlorophyll b into their respective chlorophyllide compounds.

In one embodiment, a polypeptide as disclosed herein has pyropheophytinase activity, pheophytinase activity, and chlorophyllase activity.

Determination of pyropheophytin, pheophytin, chlorophyll and the reaction products pyropheophorbide, pheophorbide, chlorophyllide can be performed by HPLC as disclosed in the Examples.

A polypeptide may be derivable from any suitable origin, for instance from plant, algae or cyanobacteria. A polypeptide as disclosed herein may be derived from plant, for instance from *Hordeum* sp., or *Triticum* sp., for instance *Hordeum vulgare* or *Triticum aestivum*. A polypeptide as disclosed herein may also be generated using standard molecular techniques e.g. de novo synthesis.

A polypeptide having decolorase activity such as pyropheophytinase activity as disclosed herein may be an isolated, a pure, recombinant, synthetic or a variant polypeptide. A polypeptide as disclosed herein may be purified. Purification of proteins can be performed by several methods known to a person skilled in the art.

A variant polypeptide of a polypeptide having pyropheophytinase activity as disclosed herein may be a polypeptide that has at least 85%, 86%, 87%, 88%, 89%, 90%, 91%, 92%, 93%, 94%, 95%, 96%, 97%, 98%, or at least 99% identity to amino acids 1 to 318 of SEQ ID NO: 1, or to amino acids 2 to 318 of SEQ ID NO:1.

A polypeptide having pyropheophytinase activity as disclosed herein may be a polypeptide, for instance a variant polypeptide, which, when aligned with an amino acid sequence according to SEQ ID NO: 1 comprises a substitution, deletion and/or insertion at one or more amino acid positions as compared to SEQ ID NO: 1. For instance, a polypeptide as disclosed herein may be a polypeptide, which when aligned with a polypeptide of SEQ ID NO:1 comprises 1, 2, 3, 4, 5, 6, 7, 8, 9, 10, 11 or 12, or more amino substitutions, deletions and/or insertions as compared to SEQ ID NO: 1, whereby the polypeptide still has the activity or function of a polypeptide as disclosed herein. The skilled person will appreciate that these minor amino acid changes in a polypeptide as disclosed herein may be present (for example naturally occurring mutations) or made (for example using r-DNA technology) without loss of the protein function or activity. In case these mutations are present in a binding domain, active site, or other functional domain of the polypeptide a property of the polypeptide may change but the polypeptide may keep its activity. In case a mutation is present which is not close to the active site, binding domain, or other functional domain, less effect may be expected.

A polypeptide as disclosed herein may be encoded by any suitable polynucleotide sequence, as long as the polypeptide exhibits pyropheophytinase activity as disclosed herein. Typically, a polynucleotide sequence encoding a polypeptide having pyropheophytinase activity as disclosed herein is a codon optimized sequence, or a codon pair optimized sequence for expression of the polypeptide in a particular host cell.

Compositions

In one aspect, the present disclosure relates to a composition comprising a polypeptide as disclosed herein.

A composition as disclosed herein, may comprise a carrier, an excipient, or other compounds. Typically, a composition, or a formulation, comprises a compound with which a polypeptide having pyropheophytinase activity may be formulated. Suitable formulations include liquid formulations, such as emulsions, suspensions and solutions, pastes, gels, granules and freeze-dried or spray-dried powders.

An excipient as used herein is an inactive substance formulated alongside with a polypeptide as disclosed herein, for instance sucrose or lactose, glycerol, sorbitol or sodium chloride. A composition comprising a polypeptide as disclosed herein may be a liquid composition or a solid composition. A liquid composition usually comprises water. When formulated as a liquid composition, the composition usually comprises components that lower the water activity, such as glycerol, sorbitol or sodium chloride (NaCl). A solid composition comprising a polypeptide as disclosed herein may comprise a granulate comprising the polypeptide or the composition comprises an encapsulated polypeptide in liquid matrices like liposomes or gels like alginate or carrageenans. There are many techniques known in the art to encapsulate or granulate a polypeptide or enzyme (see for instance G. M. H. Meesters, "Encapsulation of Enzymes and Peptides", Chapter 9, in N. J. Zuidam and V. A. Nedović (eds.) "Encapsulation Technologies for Active Food Ingredients and food processing" 2010).

A composition as disclosed herein may also comprise a carrier comprising a polypeptide as disclosed herein. For instance, a polypeptide as disclosed herein can be immobilized on silica. A polypeptide as disclosed herein may be bound or immobilized to a carrier by known technologies in the art.

A composition comprising a polypeptide having pyropheophytinase activity as disclosed herein may comprise one or more further enzymes, for instance a lipase, such as phospholipase, for instance phospholipase A, B and/or C, a chlorophyllase, pheophytinase and/or a pyropheophytinase. A further enzyme may be a phospholipase C (PLC), a phosphatidyl-inositol PLC and/or a phospholipase A, such as a phospholipase A1 or a phospholipase A2.

A composition comprising a polypeptide having pyropheophytinase activity as disclosed herein may comprise cell fractions for instance cell fractions from a host cell wherein the polypeptide having pyropheophytinase activity has been produced. Cell fractions may be generated by various methods for instance after disruption of the host cell by sonification and/or use of glass beads.

The present disclosure also relates to a process for preparing a composition comprising a polypeptide as disclosed herein, which may comprise spray drying a fermentation medium comprising the polypeptide, or granulating, or encapsulating a polypeptide as disclosed herein, and preparing the composition.

Nucleic Acids, Expression Vectors, and Recombinant Host Cells

The present disclosure also relates to a nucleic acid which has at least 80%, 85%, 86%, 87%, 88%, 89%, 90%, 91%, 92%, 93%, 94%, 95%, 96%, 97%, 98%, or at least 99% identity or which has 100% identity to a nucleic acid sequence encoding a polypeptide as disclosed herein. A nucleic acid as disclosed herein may be a nucleic acid which has at least 80%, 85%, 86%, 87%, 88%, 89%, 90%, 91%, 92%, 93%, 94%, 95%, 96%, 97%, 98% or at least 99% identity to SEQ ID NO: 2. A nucleic acid as disclosed herein may comprise or contain SEQ ID: NO:2. A nucleic acid as disclosed herein may further comprise a promotor sequence and/or other control sequence.

A nucleic acid encoding a polypeptide having pyropheophytinase activity as disclosed herein may be a codon optimized, or a codon pair optimized sequence for expression of a polypeptide as disclosed herein in a particular host cell. A host cell may for instance be *Pseudomonas* sp, for instance *Pseudomonas fluorescens.*

In one other embodiment of the present invention a nucleic acid is disclosed that is an isolated, pure, recombinant, synthetic or variant nucleic acid of the nucleic acid of SEQ ID NO: 2. A variant nucleic acid sequence may for instance have at least 80%, 85% 86%, 87%, 88%, 89%, 90%, 91%, 92%, 93%, 94%, 95%, 96%, 97%, 98%, or at least 99% sequence identity to SEQ ID NO: 2.

The present invention also relates to an expression vector comprising a nucleic acid as disclosed herein, wherein the nucleic acid is operably linked to one or more control sequence(s) that direct expression of the polypeptide in a host cell.

There are several ways of inserting a nucleic acid into a nucleic acid construct or an expression vector which are known to a skilled person in the art, see for instance Sambrook & Russell, Molecular Cloning: A Laboratory Manual, 3rd Ed., CSHL Press, Cold Spring Harbor, NY, 2001. It may be desirable to manipulate a nucleic acid encoding a polypeptide of the present invention with control sequences, such as promoter and terminator sequences.

A promoter may be any appropriate promoter sequence suitable for a eukaryotic or prokaryotic host cell, which shows transcriptional activity, including mutant, truncated, and hybrid promoters, and may be obtained from polynucleotides encoding extracellular or intracellular polypeptides either endogenous (native) or heterologous (foreign) to the cell. The promoter may be a constitutive or inducible promoter. Preferably, the promoter is an inducible promoter, for instance a starch inducible promoter.

Promoters suitable in filamentous fungi are promoters which may be selected from the group, which includes but is not limited to promoters obtained from the polynucleotides encoding *A. oryzae* TAKA amylase, *Rhizomucor miehei* aspartic proteinase, *Aspergillus* gpdA promoter, *A. niger* neutral alpha-amylase, *A. niger* acid stable alpha-amylase, *A. niger* or *A. awamori* glucoamylase (glaA), *A. niger* or *A. awamori* endoxylanase (xlnA) or beta-xylosidase (xlnD), *T. reesei* cellobiohydrolase I (CBHI), *R. miehei* lipase, *A. oryzae* alkaline protease, *A. oryzae* triose phosphate isomerase, *A. nidulans* acetamidase, *Fusarium venenatum* amyloglucosidase (WO 00/56900), *Fusarium venenatum* Dania (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the polynucleotides encoding *A. niger* neutral alpha-amylase and *A. oryzae* triose phosphate isomerase), and mutant, truncated, and hybrid promoters thereof.

Promoters suitable in bacterial hosts are promoters which may be selected from the group of the *E. coli* lac promoter, the aroH promoter, the araBAD promoter, the T7 promoter, the trc promoter, the tac promoter and the trp promoter. Other examples of promoters are the promotor of the *Streptomyces coelicolor* agarase gene (dagA), the promoter of the *Bacillus lentus* alkaline protease gene (aprH), the promoter of the *Bacillus licheniformis* alkaline protease gene (subtilisin Carlsberg gene), the promoter of the *Bacillus subtilis* levansucrase gene (sacB), the promoter of the *Bacillus subtilis* alpha amylase gene (amyE), the promoter of the *Bacillus licheniformis* alpha amylase gene (amyL), the promoter of the *Bacillus stearothermophilus* maltogenic amylase gene (amyM), or the promoter of the *Bacillus amyloliquefaciens* alpha-amylase gene (amyQ). Another example is a "consensus" promoter having the sequence TTGACA for the "−35" region and TATAAT for the "−10" region.

The present invention also relates to a recombinant host cell comprising a nucleic acid as disclosed herein, or an expression vector as disclosed, wherein the nucleic acid is heterologous to the host cell. A recombinant host cell as disclosed herein may be a host cell wherein the nucleic acid and the encoding polypeptide having pyropheophytinase activity as disclosed herein are heterologous to the host cell.

A host cell as disclosed herein may be any suitable microbial, plant or insect cell. A suitable host cell may be a fungal cell, for instance from the genus *Acremonium, Aspergillus, Chrysosporium, Fusarium, Penicillium, Rasamsonia, Trichoderma, Saccharomyces, Kluyveromyces, Pichia*, for instance *Aspergillus niger, Aspergillus awamori, Aspergillus foetidus, A. oryzae, A. sojae, Rasamsonia emersonii Chrysosporium lucknowense, Fusarium oxysporum, Trichoderma reesei* or, *Saccharomyces cerevisiae, Kluyveromyces lactis*, or *Pichia pastoris.*

A host cell may be a prokaryotic cell, such as a bacterial cell. The term "bacterial cell" includes both Gram-negative and Gram-positive microorganisms. Suitable bacteria may be from the genus *Escherichia, Pseudomonas, Bacillus, Enterobacter, Lactobacillus, Lactococcus*, or *Streptomyces*. A bacterial cell may be from the species *B. subtilis, B. amyloliquefaciens, B. licheniformis, B. puntis, B. megaterium, B. halodurans, B. pumilus, Pseudomonas zeaxanthinifaciens, Pseudomonas fluorescens*, or *E. coli.*

A suitable bacterial host cell may for instance be a *Pseudomonas* sp., such as *Pseudomonas fluorescens.*

Methods of Polypeptide Production

The present disclosure also relates to a method for producing a polypeptide having pyropheophytinase activity, comprising cultivating a host cell as disclosed herein in a suitable fermentation medium under conditions that allow expression of the polypeptide and producing the polypeptide. A skilled person in the art understands how to perform a process for the production of a polypeptide as disclosed herein depending on a host cell used, such as pH, temperature and composition of a fermentation medium. Host cells can be cultivated in shake flasks, or in fermenters having a volume of 0.5 or 1 litre or larger to 10 to 100 or more cubic metres. Cultivation may be performed aerobically or anaerobically depending on the requirements of a host cell. In the event the host cell is *Pseudomonas* sp., for instance *Pseudomonas fluorescens*, cultivation of the host cell is performed under aerobic conditions.

Advantageously, a polypeptide as disclosed herein is recovered or isolated from the fermentation medium, for instance by centrifugation or filtration known to a person skilled in the art. Recovery of a polypeptide having pyropheophytinase activity may also comprise disruption of the cells wherein the polypeptide is produced. Disruption of cells can be performed using glass beads and, or sonification known to a person skilled in the art.

Processes for Treating Oils Comprising Chlorophyll Substrates

In one embodiment, the present disclosure also relates to a process for treating an oil, comprising a chlorophyll substrate, such a pyropheophytin. The process comprises contacting the oil comprising a chlorophyll substrate such a pyropheophytin with a polypeptide having decolorase activity as disclosed herein, or with a composition comprising a polypeptide as disclosed herein above. In one embodiment, the polypeptide as disclosed herein has pyropheophytinase activity. In another embodiment, the polypeptide has pheophytinase activity. In another embodiment, the polypeptide has pyropheophytinase activity and pheophytinase activity. In another embodiment, the polypeptide has pyropheophytinase activity, pheophytinase activity, and chlorophyllase activity.

As discussed herein, a polypeptide having pyropheophytinase activity is capable of hydrolyzing pyropheophytin into pyropheophorbide, a polypeptide having pheophytinase activity is capable of hydrolyzing the pheophytin into pheophorbide, and a polypeptide having chlorophyllase activity is capable of hydrolyzing chlorophyll into chlorophyllide. Thus, in one embodiment, the treatment process of the present disclosure may reduce the level of one or more chlorophyll substrate in the oil. In various embodiments, the chlorophyll substrate may be chlorophyll, pheophytin, and/or pyropheophytin. For example, the treatment may reduce the total concentration of chlorophyll substrates in the oil by at least 5%, at least 10%, at least 20%, at least 30%, at least 40%, at least 50%, at least 60%, at least 70%, at least 80%, at least 90%, at least 95%, at least 99%, or by 100% by weight, compared to the total concentration of chlorophyll substrate (by weight) present in the oil prior to treatment. The reduction in total concentration of chlorophyll substrate may be the result of conversion of pyropheophytin into pyropheophorbide, pheophytin into pheophorbide, and/or chlorophyll into chlorophyllide.

In another embodiment, the chlorophyll substrate in the oil comprises pyropheophytin, and at least a portion of the pyropheophytin is converted into pyropheophorbide as a result of the treatment. For example, the treatment may reduce the total concentration of pyropheophytin in the oil by at least 5%, at least 10%, at least 20%, at least 30%, at least 40%, at least 50%, at least 60%, at least 70%, at least 80%, at least 90%, at least 95%, at least 99%, or by 100% by weight, compared to the total concentration of pyropheophytin (by weight) present in the oil prior to treatment. The reduction in total concentration of pyropheophytin may be the result of conversion of pyropheophytin into pyropheophorbide. In another embodiment, the chlorophyll substrate in the oil comprises pheophytin, and at least a portion of the pheophytin is converted into pheophorbide as a result of the treatment. For example, the treatment may reduce the total concentration of pheophytin in the oil by at least 5%, at least 10%, at least 20%, at least 30%, at least 40%, at least 50%, at least 60%, at least 70%, at least 80%, at least 90%, at least 95%, at least 99%, or by 100% by weight, compared to the total concentration of pheophytin (by weight) present in the oil prior to treatment. The reduction in total concentration of pheophytin may be the result of conversion of pheophytin into pheophorbide. In such embodiments, the polypeptide exhibits pheophytinase activity.

In another embodiment, the chlorophyll substrate in the oil comprises chlorophyll, and at least a portion of the chlorophyll is converted into chlorophyllide as a result of the treatment. For example, the treatment may reduce the total concentration of chlorophyll in the oil by at least 5%, at least 10%, at least 20%, at least 30%, at least 40%, at least 50%, at least 60%, at least 70%, at least 80%, at least 90%, at least 95%, at least 99%, or by 100% by weight, compared to the total concentration of chlorophyll (by weight) present in the oil prior to treatment. The reduction in total concentration of chlorophyll may be the result of conversion of chlorophyll into chlorophyllide. In such embodiments, the polypeptide exhibits chlorophyllase activity.

An oil comprising pyropheophytin, pheophytin, and/or chlorophyll may further comprise, other substrates such as phospholipids. Optionally, a process for treating an oil as disclosed herein further comprises removal of phospholipids, as described hereinafter.

Any oil comprising a chlorophyll substrate may be treated in accordance with the present process in order to remove one or more undesirable chlorophyll substrate from the oil. The oil may be a triacylglycerol-based oil, including various vegetable- or algal-based oils. In one embodiment, suitable oils that may be used in connection with the present treatment include, but are not limited to the following: canola oil, castor oil, coconut oil, coriander oil, corn oil, cottonseed oil, hazelnut oil, hempseed oil, linseed oil, mango kernel oil, meadowfoam oil, neat's foot oil, olive oil, palm oil, palm kernel oil, palm olein, peanut oil, rapeseed oil, rice bran oil, safflower oil, sasanqua oil, sesame oil, soybean oil, sunflower or sunflower seed oil, tall oil, tsubaki oil, vegetable oil, and oil from algae. In one embodiment, an oil that can be treated in accordance with the present disclosure is selected from the group consisting of canola oil, corn oil, olive oil, palm oil, palm kernel oil, peanut oil, rapeseed oil, rice bran oil, sesame oil, soybean oil and sunflower seed oil. In one embodiment, the oil is an oil from algae.

Contacting an oil comprising one or more chlorophyll substrate with a polypeptide having decolorase activity may be performed during any suitable time and at any suitable pH and temperature. Said contacting may be performed at a pH and temperature which are applied during degumming of a triacylglycerol oil. A suitable pH may be from pH 2 to pH 10, for instance from pH 3 to pH 9, from pH 4 to pH 8, from pH 5 to pH 7, from pH 5 to 8, or from pH 6.5 to 7.5. In one embodiment, the polypeptide is contacted with the oil at a pH of from 4.0 to 7.5, or from 4.5 to 8.0, or from 4.5 to 7.0. In one embodiment, the polypeptide is contacted with the oil at a pH of from 4.0 to 5.0, or more specifically at a pH of 4.5. In another embodiment, the polypeptide is contacted at a pH of 7.0.

A suitable temperature for contacting an oil comprising one or more chlorophyll substrate with a polypeptide having decolorase activity as disclosed herein may be from 10° C. to 90° C., for instance from 20° C. to 80° C., from 30° C. to 70° C., from 45° C. to 70° C., from 40° C. to 60° C., or from 50° C. to 65° C.

For instance, contacting an oil comprising one or more chlorophyll substrate with a polypeptide having decolorase activity may be performed at a pH of from 5 to 8, and a temperature of from 40° C. to 60° C., or at a pH of from 4.5 to 7.0 and a temperature of from 40° C. to 60° C., or at a pH of 7.0 and a temperature of from 45° C. to 70° C., or at a pH of 7.0 and a temperature of from 50° C. to 65° C.

The polypeptide having decolorase activity may be dosed into the oil comprising a chlorophyll substrate in any suitable amount. For example, the polypeptide may be dosed in a range of 1 to 50 U/gram of treated oil, such as from 1.4 to 50 U/gram of treated oil, or 5 to 50 U/gram of treated oil. One unit is defined in accordance with the enzyme activity taught in the examples below.

Surprisingly, it was found that a polypeptide having decolorase, such as pyropheophytinase activity as disclosed herein converts a higher amount of chlorophyll substrates to chlorophyll products under acidic and caustic conditions as compared to a reference polypeptide. A reference polypeptide is a polypeptide comprising the amino acid sequence according to SEQ ID NO: 12. SEQ ID NO: 12 comprises *Chlamydomonas reinhardtii* chlorophyllase having pyropheophytinase activity.

Contacting an oil comprising one or more chlorophyll substrate with a polypeptide having decolorase activity may be performed during oil degumming. Oil degumming comprises several processing steps, such as pressing and/or hexane extraction, degumming, for instance in the presence of degumming enzymes such as phospholipases as disclosed in WO2005/086900 or WO2011/046812, refining, bleaching and deodorization. Contacting an oil comprising one or more chlorophyll substrate with a polypeptide having pyropheophytinase activity, pheophytinase activity, and/or chlorophyllase activity may be performed during a bleaching step in oil degumming processing, as described in more detail hereinafter.

Contacting a polypeptide having pyropheophytinase activity with an oil, such as a triacylglycerol oil or an algal oil, may comprise dispersing an aqueous solution comprising the polypeptide as disclosed herein in the oil. An oil that is treated with a polypeptide having pyrpheohytinase activity typically comprises 0.5 to 10 w/w % of water, for instance 1 to 10 w/w % of water, 1 to 5 w/w % of water, 2 to 8 w/w % of water, 2 to 4 w/w % of water, 3 to 6 w/w % of water, 0.5 to 5 w/w % of water, 1 to 3 w/w %, 1.5 to 2 w/w % of water, or 5 w/w % water.

The polypeptide may be contacted with the oil for a period of from 5 minutes to 24 hours, from 10 minutes to 12 hours, from 15 minutes to 10 hours, from 0.5 to 24 hours, from 1 to 12 hours, from 1.5 to 6 hours, or from 2 to 4 hours. In one embodiment, the polypeptide may be contacted with the oil for 2 hours. After said contacting, a water phase and an oil phase are usually separated.

An oil that is treated in a process as disclosed herein may be a crude non-degummed, degummed (water degummed, enzyme degummed, or acid degummed), caustic refined or a caustic refined and water washed oil or a water degummed oil. In one particular embodiment, the oil comprises a non-degummed crude oil. A crude oil usually is an oil that is mechanically pressed, or solvent extracted, and wherein the oil usually contains Free Fatty Acids (FFA) and phospholipids. A degummed oil is an oil wherein the majority of phospholipids has been removed from a crude oil. Usually a degummed oil comprises between 0.5 to 200 ppm atomic phosphorous, such as between 1 and 100 ppm atomic phosphorous, such as between 5 and 50 ppm atomic phosphorous. A refined oil is an oil where the FFA have been neutralized by a caustic treatment and removed. A caustic treatment of oil usually comprises treating an oil with sodium hydroxide.

Contacting a polypeptide having decolorase (eg. pyropheophytinase) activity as disclosed herein with an oil, for instance during degumming of an oil may be performed at any suitable temperature, for instance at a temperature from 45 to 70° C., including from 50 to 65° C.

Contacting a polypeptide having decolorase (eg. pyropheophytinase) activity as disclosed herein with an oil, for instance during degumming of an oil may be performed at any suitable pH, such as pH of from 3.5 to 8.0, for instance pH 4 to 7.5, for instance pH 4.5 to 7.0

In one embodiment, the treatment process disclosed herein further comprises subjecting the oil to water degumming. As discussed herein, water degumming is usually applied to crude oils containing a high amount of hydratable phospholipids. Due to its mild characteristics, the phospholipids obtained can be used as lecithin (a natural emulsifier). The oil obtained from this process is generally referred to in the industry as being "degummed," despite being only partially degummed.

Thus, in one aspect, the treatment process of the present disclosure comprises contacting an oil (e.g., a non-degummed crude oil), comprising a chlorophyll substrate, with water and a polypeptide of the present disclosure. Typically, the temperature of the oil is from 45 to 70° C., including from 50 to 65° C. The water may be added in an amount of from 1 to 5 w/w %, including from 2 to 4 w/w %. The polypeptide may be dosed in an amount of 1 to 50 U/gram of treated oil, such as from 1.4 to 50 U/gram of treated oil, or 5 to 50 U/gram of treated oil. The polypeptide as disclosed herein and water may be added as a single composition, or the polypeptide may be added separately from the water. Typically, no acid or base is added to the resulting mixture, and the process proceeds at a neutral pH (e.g., around pH 7.0). Following contact with the polypeptide and water, the oil may optionally be mixed using a shear mixer. The oil is subsequently incubated with stirring (e.g., using a continuously stirred reactor) for from 0.5 to 24 hours, or 1 to 12 hours, or 1.5 to 6 hours, or 2 to 4 hours, which aids in hydration of phospholipids present in the oil. Following incubation and stirring, the oil is heated to a temperature of from 70 to 85° C. The resulting oil may be separated by settling, filtration, or the industrial practice of centrifugation. The centrifuge yields two streams, water degummed oil and wet gums.

In another embodiment, the treatment process disclosed herein further comprises subjecting an oil to enzyme assisted water degumming. As discussed herein, enzyme assisted water degumming is usually applied to crude oils containing a high amount of hydratable phospholipids where the goal is to react all of the hydratable phospholipids and convert them into diacylglycerols increasing the oil yield, while maintaining the no-hydratable phospholipids in the oil. Enzymes utilized for this process include phospholipase C (PLC) and phosphatidyl inositol-phospholipase (PI-PLC).

Thus, in one aspect, the treatment process of the present disclosure comprises contacting an oil (e.g., a non-degummed crude oil), comprising a chlorophyll substrate with water, a polypeptide of the present disclosure, and an additional enzyme. The additional enzyme may be selected from the group consisting of PLC, PI-PLC and combinations thereof. In one embodiment, the additional enzyme includes both PLC and PI-PLC. Typically, the temperature of the oil is from 45 to 70° C., including from 50 to 65° C. The water may be added in an amount of from 1 to 5 w/w %, including from 2 to 4 w/w %. The polypeptide may be dosed in an amount of 1 to 50 U/gram of treated oil, such as from 1.4 to 50 U/gram of treated oil, or 5 to 50 U/gram of treated oil. The PLC (e.g., Purifine PLC) may be added in an amount of from 50 to 500 ppm, including from 100 to 400 ppm, or from 150 to 250 ppm. The PI-PLC may be added in an amount of from 50 to 500 ppm, including from 100 to 400 ppm, or from 150 to 250 ppm. In one embodiment, the additional enzyme is Purifine 4G, which contains both PLC and PI-PLC. In this embodiment, the Purifine 4G may be added in an amount of from 50 to 500 ppm, including from 100 to 400 ppm, or from 150 to 250 ppm. The polypeptide as disclosed herein, additional enzymes, and water may be added as a single composition, or the polypeptide as disclosed herein, additional enzymes, and water may be added separately. Typically, no acid or base is added to the resulting mixture, and the process proceeds at a neutral pH (e.g., around pH 7.0). Following contact with the polypeptide, additional enzymes, and water, the composition may optionally be mixed using a shear mixer. A suitable shear mixer is the continuous shear mixer IKA Dispax Reactor. The composition is subsequently incubated with stirring (e.g., using a continuously stirred reactor) for from 0.5 to 24 hours, or 1 to 12 hours, or 1.5 to 6 hours, or 2 to 4 hours, which aids in conversion of PC, PE, and PI to diacylglycerols in the oil. Following incubation and stirring, the composition is heated to a temperature of from 70 to 85° C., such as 85° C. The resulting composition may be separated by settling, filtration, or the industrial practice of centrifugation. The centrifuge yields two streams, water degummed oil and heavy phase (containing water, denatured protein, and phosphor-compounds).

In another embodiment, the treatment process disclosed herein further comprises subjecting the oil to enzyme degumming. Enzyme degumming may be applied to crude oils or to oils that have been degummed previously by a different method, such as water degumming, enzyme assisted water degumming, or acid degumming. A processor who wishes to produce lecithin for the food or industrial market may water degum the oil prior to further processing. The destruction of the phospholipids is unacceptable in lecithin applications.

Thus, in one aspect, the treatment process of the present disclosure comprises contacting a composition, such as an oil (e.g., a crude oil or previously degummed oil), comprising a chlorophyll substrate, with a polypeptide of the present disclosure. The pH of the oil may be adjusted prior to contacting with the polypeptide, for example by addition of an acid (e.g., citric or phosphoric acid) in an amount of from 100 to 1000 ppm, including 500 ppm. Typically, the pH is adjusted to a pH of from 4.5 to 8.0, including from 4.5 to 7.0.

Typically, the temperature of the oil is from 70 to 85° C. at the time of pH adjustment. Following acid addition, the resulting oil may be mixed for from 5 minutes to 24 hours, depending on the type of mixer (e.g., high shear, agitator, etc.). One skilled in the art will understand that lower mixing times will be needed when high shear mixers are used, while higher mixing times will be needed when less shear is applied (e.g., when using a simple agitator). Following pH adjustment, the composition (e.g., oil) is cooled to from 45 to 70° C., including from 50 to 65° C., and water, a polypeptide of the present disclosure, and optionally an additional enzyme are added. The additional enzyme (when used) may be selected from the group consisting of PLC, PI-PLC, and combinations thereof. In one embodiment, the additional enzyme includes both PLC and PI-PLC. The water may be added in an amount of from 1 to 5 w/w %, including from 2 to 4 w/w %. The polypeptide may be dosed in an amount of 1 to 50 U/gram of treated oil, such as from 1.4 to 50 U/gram of treated oil, or 5 to 50 U/gram of treated oil. The PLC (e.g., Purifine PLC) may be added in an amount of from 50 to 500 ppm, including from 100 to 400 ppm, or from 150 to 250 ppm. The PI-PLC may be added in an amount of from 50 to 500 ppm, including from 100 to 400 ppm, or from 150 to 250 ppm. In one embodiment, the additional enzyme is Purifine 4G, which contains both PLC and PI-PLC. In this embodiment, the Purifine 4G may be added in an amount of from 50 to 500 ppm, including from 100 to 400 ppm, or from 150 to 250 ppm. The polypeptide, additional enzyme (when present), and water may be added as a single composition, or the polypeptide, additional enzymes, and water may be added separately.

Following contact with the polypeptide, additional enzyme (when present), and water, the composition may be mixed using a shear mixer. A suitable shear mixer is the continuous shear mixer IKA Dispax Reactor. Shear mixing is optional, particularly when the composition being treated is, or comprises, a crude, non-degummed oil. The composition is subsequently stirred (e.g., using a continuously stirred reactor) for from 0.5 to 24 hours, or 1 to 12 hours, or 1.5 to 6 hours, or 2 to 4 hours.

Following stirring, a phospholipase A (PLA) enzyme is added to the oil. The PLA enzyme may be a PLA1 enzyme and/or PLA2 enzyme. In one embodiment, the enzyme is a PLA1 enzyme. Sequences of amino acids with phospholipase activity are extensively reported in the art, including phospholipids having activity in triacylglycerol oils. Commercial PLA1 enzymes with phospholipase activity include Lecitase® Ultra and QuaraLowP. Commercial PLA2 enzymes with phospholipase activity include Rohalase Xtra and LysoMax. Any suitable PLA enzyme may be PLA added may vary depending on the manufacturer and the type of continuous stirred-tank reactor used. Following addition of the PLA enzyme, the oil may be mixed using a shear mixer. A suitable shear mixer is the continuous shear mixer IKA Dispax Reactor. The oil is subsequently incubated with stirring (e.g., using a continuously stirred reactor). The oil may be incubated with the PLA1 enzyme allowed to react for from 1 to 8 hours, or 2 to 7 hours, or 3 to 6 hours. Following incubation and stirring, the oil is heated to a temperature of from 70 to 85° C., such as 85° C. Reaction times may vary, depending on the PLA dosage and the level of non-hydratable phospholipids (NHPs) (e.g., Ca and Mg salts of phosphatidic acid) present. The resulting oil may be separated by settling, filtration, or the industrial practice of centrifugation.

In another embodiment, the treatment process of the present disclosure comprises contacting an oil, in particular a once refined oil, comprising a chlorophyll substrate, with a polypeptide of the present disclosure. Typically, the temperature of the oil is from 45 to 70° C., including from 50 to 65° C. The polypeptide may be dosed in an amount of 1 to 50 U/gram of treated oil, such as from 1.4 to 50 U/gram of treated oil, or 5 to 50 U/gram of treated oil. Water may be added to the oil in an amount of from 1 to 10 w/w %, including from 2 to 8 w/w %, or 3 to 6 w/w %, or 5 w/w %. The polypeptide and water may be added as a single composition, or the polypeptide may be added separately from the water. Typically, no acid or base is added to the resulting mixture, and the process proceeds at a neutral pH (e.g., pH 7.0). Following contact with the polypeptide and water, the oil may be mixed using a shear mixer. A suitable shear mixer is the continuous shear mixer IKA Dispax Reactor. The oil is incubated with stirring for from 1.5 to 3 hours, including 2 hours. Following incubation and stirring, the oil is heated to a temperature of from 70 to 85° C. The resulting oil may be separated by settling, filtration, or the industrial practice of centrifugation.

In another embodiment a process for treating an oil comprising a chlorophyll derivative as disclosed herein may further comprise removal of pyropheophorbide, and/or pheophorbide. In one embodiment, a process for treating an oil comprising a chlorophyll derivative as disclosed herein may further comprise removal of chlorophyllide, pyropheophorbide, and/or pheophorbide. Pyropheophorbide, pheophorbide, and/or chlorophyllide can be removed during a water wash of the oil, during a chemical refining step (addition of water to remove excess soap), or by using a solid adsorbent such as silica or in the deodorization step, which is known to a person skilled in the art.

In one embodiment, a process for treating an oil comprising a chlorophyll derivative, such a pyropheophytin, may further comprise treating the oil with an additional enzyme selected from the group consisting of a phospholipase, a chlorophyllase, a pheophytinase, a pyropheophytinase, and combinations thereof. A suitable phospholipase may be a phospholipase A, phospholipase B and/or phospholipase C or any suitable combination of these enzymes. Treating the oil with a phospholipase, so-called enzymatic degumming, reduces the phospholipid content in the oil, resulting in a lower atomic phosphorous content in the oil.

The present disclosure also relates to an oil (e.g, a triacylglycerol oil, vegetable oil, oil from algae, etc.) obtainable by a process as disclosed herein. An oil, which may be a triacylglycerol oil obtainable by a process as disclosed herein may comprise a polypeptide having decolorase activity, such as pyropheophytinase activity as disclosed herein.

FIGURES

FIG. 1: Overview of the conversion of chlorophyll into pheophytin and pyropheophytin and into the respective reaction products chlorophyllide, pheophorbide and pyropheophorbide. The A compounds are shown, which have a methyl group at the C7 position. B compounds have an aldehyde in the C7 group instead of a methyl group. Structures are taken from PubChem, NCBI.

FIG. 2: HPLC results of incubation pheophytin a and b and pyropheophytin a and b with different putative chlorophyllases at pH 7 and 50° C., for 24 hours. The amounts of the substrates pheophytin a and b and pyropheophytin a and b and the reaction products pheophorbide a and b and pyropheophorbide a and b are given as peak surface areas. The first two columns show the sum of reaction products and substrates. "nd" means: not detectable.

FIG. 3: HPLC results of incubation pheophytin a and b and pyropheophytin a and b with different putative chlorophyllases at pH 5 and 50° C., for 24 hours. The amounts of the substrates pheophytin a and b and pyropheophytin a and b and the reaction products pheophorbide a and b and pyropheophorbide a and b are given as peak surface areas. The first two columns show the sum of reaction products and substrates. "nd" means: not detectable.

FIG. 4: a) Chlorophyll derivatives b) Phosphor compounds in canola oil after 24 h incubation with CHL26 enzyme from *Hordeum vulgare* or the reference enzyme ELDC94 from *Chlamydomonas reinhardtii.*

FIG. 5: a) Chlorophyll derivatives, and b) Phosphor compounds in canola oil and soy bean after several incubations with CHL26 enzyme from *Hordeum vulgare* and/or the reference enzyme ELDC94 from *Chlamydomonas reinhardtii*, under different reaction conditions and c) chlorophyll derivatives in the obtained gums.

FIG. 6: Chlorophyll derivatives in canola oil and soybean oil after caustic refining and after incubation with CHL26 enzyme from *Hordeum vulgare* or the reference enzyme ELDC94 from *Chlamydomonas reinhardtii*

Figure 7:
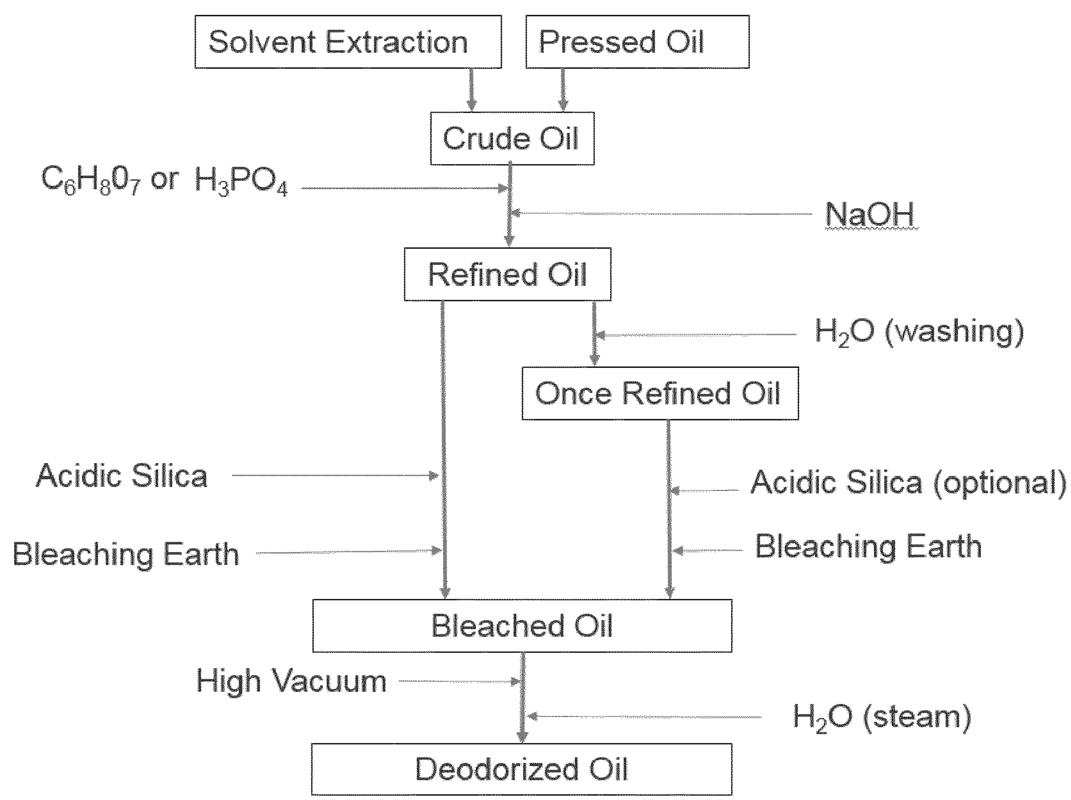

FIG. 7: Schematic presentation of a chemical refinery process for triacylglycerol based oils. A process of solvent extraction and/or pressing on an oilseed (rapeseed or soybean), oil fruit plant (palm), or single cell source (algal) to obtain a crude oil. The crude oil this then treated with citric or phosphoric acid to react with the non-hydratable phospholipids and then the addition of sodium hydroxide to neutralize the free fatty acids and form sodium soaps. The sodium soaps form an emulsion with the water present allowing the removal of non-hydratable phospholipids when the oil is centrifuged to produce refined oil. The refined oil may then be washed with hot water and centrifuged to remove the remaining soaps and phospholipids. Alternatively, the refined oil may be treated with acidic silica to adsorb soaps, trace metals and phospholipids. The industrial acidic silicas do not have any capacity to remove chlorophyll or chlorophyll derivatives. The oil is then treated with bleaching earth to remove the soaps, phospholipids, and chlorophyll and chlorophyll derivatives present in the oil. The final step in the deodorization step of steam distillation at elevated temperatures and vacuums of less than 5 mBar. The distillation primarily removes peroxides, aldehydes, ketones and other flavor compounds. It also destroys beta-carotene and removes the remaining free fatty acids (0.1 percent) to reach a level of 0.02 to 0.05% final Free Fatty Acid (FFA).

Figure 8:
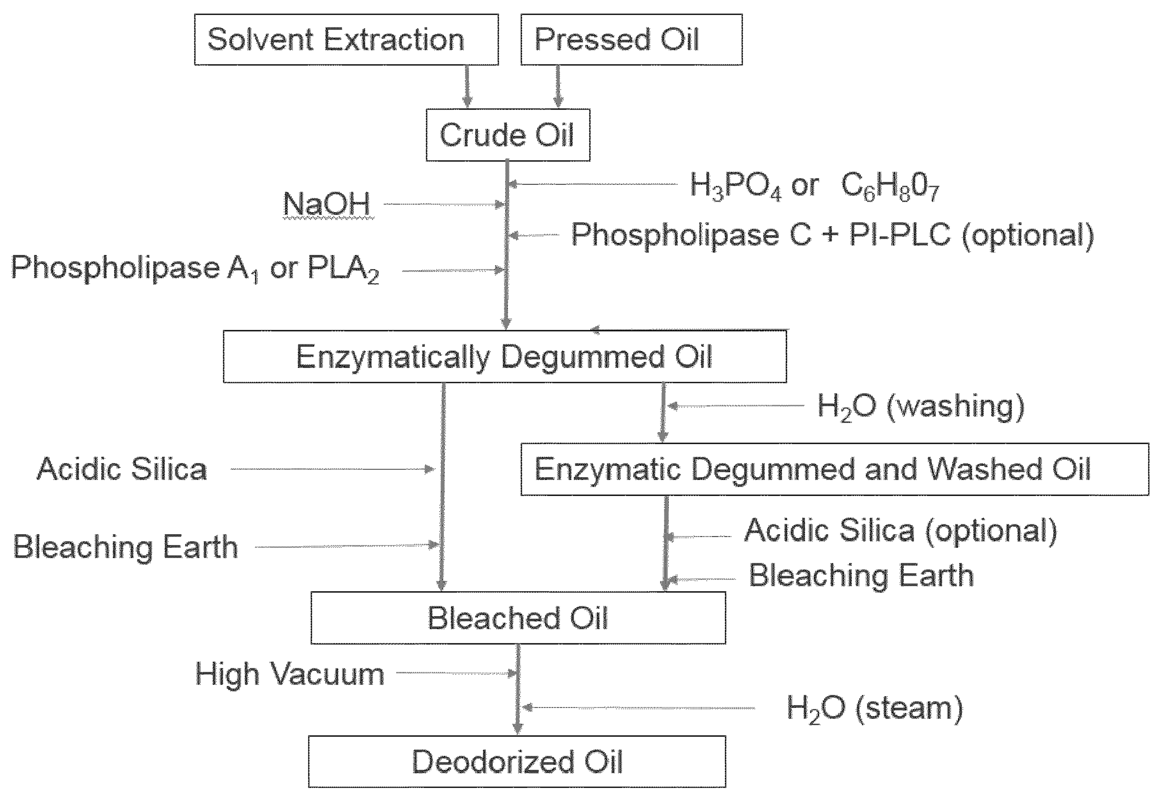

FIG. 8: Schematic presentation of an enzymatic degumming/physical refining process. The crude oil is treated with phosphoric or citric acid to enable the non-hydratable phospholipids to lose the calcium or magnesium bond to them at a pH of roughly 2. The sodium hydroxide is then added to bring the pH above 4 for citric acid or above 6 for phosphoric acid in order that the phospholipase may work and obtain a very low residual phosphorus <5 ppm) after the enzymatic reaction with the PLAs. Alternatively, the PLAs may be reacted with the PLC and/or PI-PLC to maximize the oil yield and still obtain a very low residual phosphorus allowing for physical refining. The oil is then either washed or treated with an acidic silica followed or in combination with bleaching earth. After the bleaching process with chlorophyll levels of less than 50 ppb, the oil is physically refined in the deodorizer. The high temperature steam distillation removes all of the compounds describe above in FIG. 7, but its primary purpose is the removal of FFA. The FFAs are distilled and collected in the scrubber. Very limited neutral oil is lost in the deodorization process compared to the losses associated from the emulsions formed in water degumming or chemical refining.

Figure 9:
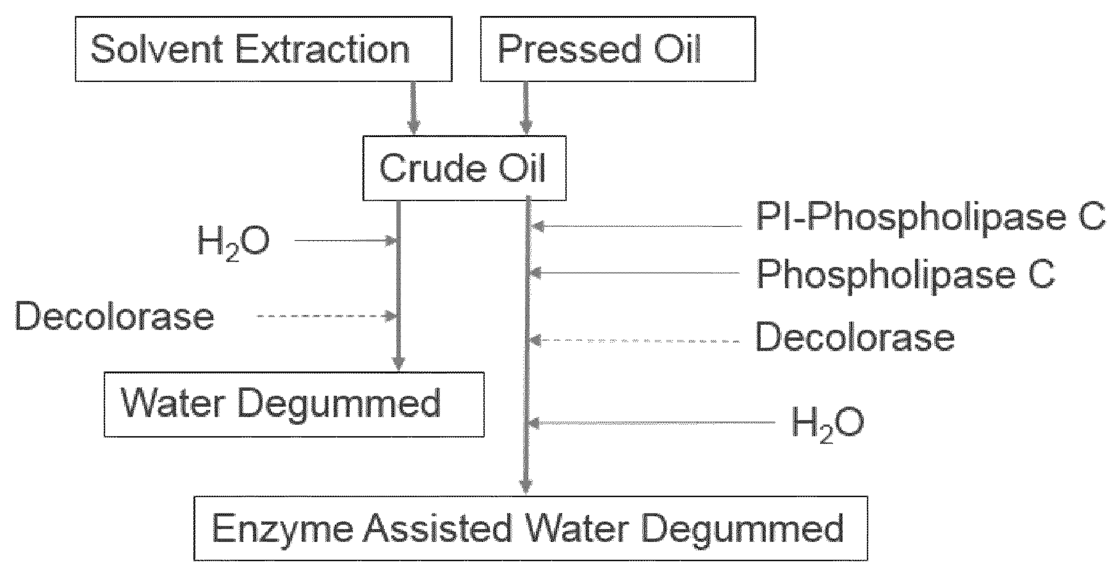

FIG. 9: Schematic presentation of the use of a decolorase enzyme in the water degumming process or the enzyme assisted water degumming process. A decolorase enzyme may be added with the water at 60° C., or with the PLC, or with the combination of PLC and PI-PLC. After two hours of incubation, the oil is heated to 70 to 85° C. and centrifuged to remove the reacted gums and reacted chlorophyll derivatives.

Figure 10:
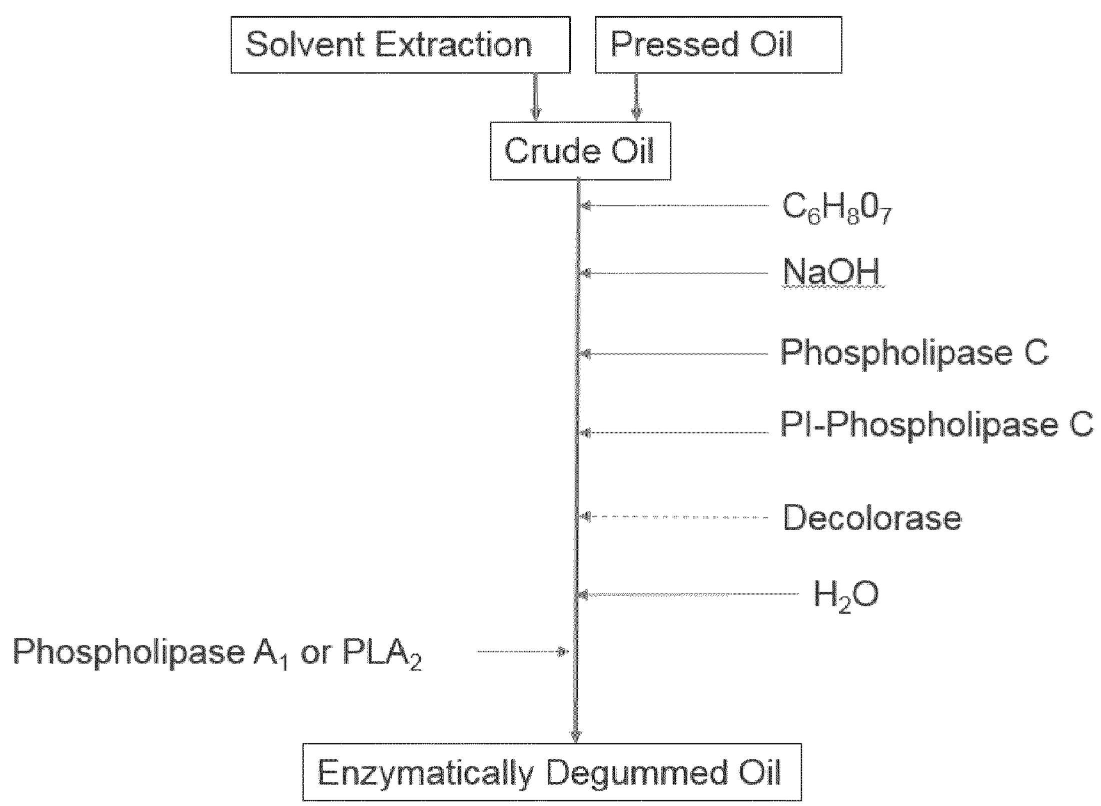

FIG. 10: Schematic presentation of an enzymatic degumming process with a decolorase enzyme. The crude oil is first treated with citric acid to a pH of roughly 2 to dissociate the bond calcium and magnesium ions, the pH is raised above 4 to enable the PLCs and Decolorase enzymes in a pH that enable them to work efficiently. 1 to 5 percent water is added for the hydrolysis reactions. After the completion of the PLCs and Decolorase incubations, a PLA1 or PLA2 may be added to react with the non-hydratable phospholipids present in the oil. After an additional incubation of 2 to 6 hours, the oil is heated to 70 to 85° C. and centrifuged to remove the reacted gums and chlorophyll derivatives producing an oil with less than 5 ppm residual phosphorus in the oil.

Figure 11:
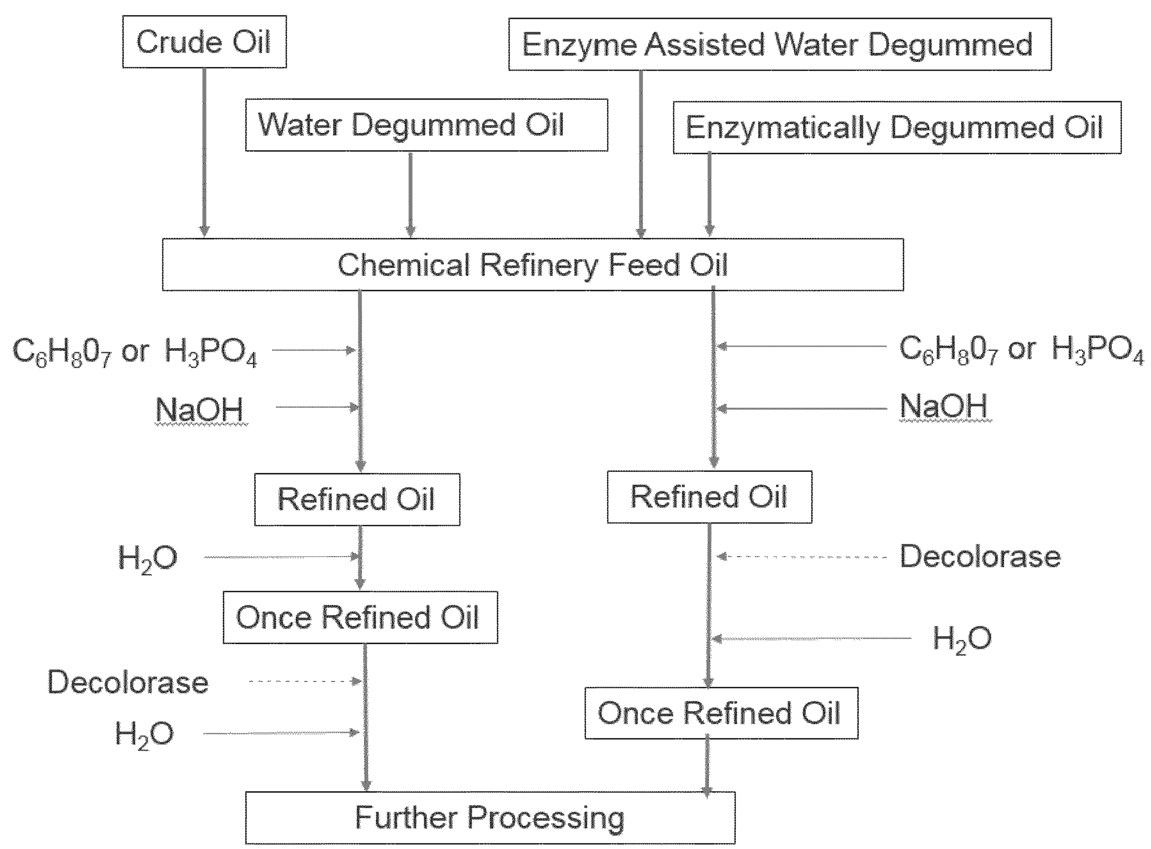

FIG. 11: Schematic presentation of a chemical refining process with a decolorase enzyme. The decolorase enzyme may not be added in the acid or caustic addition steps due to the very low pH (roughly 2) and the very high pH (roughly 14) in the early steps of the process. The decolorase enzyme must be added after the initial centrifuge step in the refined oil. It is advantageous to add the decolorase enzyme with the washing step at a temperature suitable for the enzyme (50 to 65° C.). Allow an incubation time of at least two hours followed by heating to 70 to 85° C. prior to centrifugation. The oil would then be further processed.

SEQUENCES

SEQ ID NO: 1=CHL26 polypeptide having decolorase including a pyropheophytinase activity from *Hordeum vulgare*.

```
MASAGDVFDHGRHGTSLARVEQAKNTRCSAASRVDADAQAQQSPPKPLLV

AAPCDAGEYPVVVFLHGYLCNNYFYSQLIQHVASHGFIVVCPQLYTVSGP

DTTSEINSAAAVIDWLAAGLSSKLAPGIRPNLAAVSISGHSRGGKVAFAL

GLGHAKTSLPLAALIAVDPVDGTGMGNQTPPPILAYKPNAIRVPAPVMVI

GTGLGELPRNALFPPCAPLGVSHAAFYDECAAPACHLVARDYGHTDMMDD

VTTGAKGLATRALCKSGGARAPMRRFVAGAMVAFLNKWVEGKPEWLDAVR

EQTVAAPVVLSAVEFRDE
```

SEQ ID NO: 2: Codon optimized nucleic acid sequence encoding a polypeptide having decolorase including pyropheophytinase activity from *Hordeum vulgare* CHL26 for expression in *Pseudomonas fluorescens.*

SEQ ID NO: 3; CHL25 putative chlorophyllase from *Gossypium raimondii*

SEQ ID NO: 4; CHL27 putative chlorophyllase from *Phoenix dactylifera*

SEQ ID NO: 5; CHL28 putative chlorophyllase from *Wollemia nobilis*

SEQ ID NO: 6; CHL29 putative chlorophyllase from *Cucumis sativus*

SEQ ID NO: 7; CHL30 putative chlorophyllase from *Tarenaya hassleriana*

SEQ ID NO: 8; CHL31 putative chlorophyllase from *Solanum tuberosum*

SEQ ID NO: 9; CHL32 putative chlorophyllase from *Populus trichocarpa*

SEQ ID NO: 10; CHL33 putative chlorophyllase from *Vigna radiata*

SEQ ID NO: 11; N1 Negative control, Green Fluorescent Protein (GFP)

SEQ ID NO: 12; P2, *Chlamydomonas reinhardtii* chlorophyllase having pyropheophytinase activity. SEQ ID NO: 12 is also referred to herein as ELDC94.

SEQ ID NO: 13 SpeI site and ribosome binding site

SEQ ID NO: 14 stop codon and XhoI site

EXAMPLES

Materials and Methods

General

Standard genetic techniques, such as overexpression of enzymes in the host cells, genetic modification of host cells, or hybridisation techniques, are known methods in the art, such as described in Sambrook and Russel (2001) "Molecular Cloning: A Laboratory Manual ($3^{rd}$ edition), Cold Spring Harbor Laboratory, *Cold Spring Harbor Laboratory Press*, or F. Ausubel et al, eds., "Current protocols in molecular biology", Green Publishing and Wiley Interscience, New York (1987). Water is Milli-Q water where nothing else is specified.

Analytical Methods:

pH—stoichiometric addition of acid and base to a water percentage that was added to the oil. 2 percent water in a 2000 grams reaction would be 40 grams, adding 2.0 grams of a 50 percent solution of citric acid, plus 1.6 mL of 4 M sodium hydroxide would yield a water solution with a pH of 4.5. The pH of the oil will always remain 7.

Soap—American Oil Chemists' Society Official Method Cc 13a-43, revised 2017. Free Fatty Acid—American Oil Chemists' Society Official Method Ca 5a-40, revised 2017.

Color—American Oil Chemists' Society Official Method Ce 13e-92, reapproved 2017. Utilized Tintometer's PFX-950 at 5V cell.

Phosphorus and trace metals—American Oil Chemists' Society Official Method Ca 17-01-43, revised 2017. Phospholipid Compositions For $^{31}$P NMR methods (also referred to as 31-P NMR), 10 µL of 10% DOL dispersion was dispersed in 1 mL of an aqueous solvent containing demineralized water with 10% deuterium oxide (D20, Cambridge Isotope Laboratories, DLM-4), 25 mg/mL deoxycholic acid (Sigma D2510), 5.84 mg/mL EDTA di Na (Titriplex III, Merck 108418), and 5.45 mg/mL TRIS base (Tris(hydroxymethyl) aminomethane, Merck 108387), of which the pH was adjusted to pH 9 using 4N KOH and to which 2 mg/mL TIP internal standard (tri-isopropylphosphate, Aldrich 554669) (accurately weighed) was added.

All samples were measured in a Bruker 400 MHz AvanceIII NMR spectrometer with a Prodigy BBO probe. The temperature of the probe head was set at 300K.

The measurement for quantification was performed with semi-quantitative parameters: 128 scans, 90° pulse, D1=5 sec. Values are reported in µmol/g of dry weight (DOL) of the sample.

Analysis of Coloured Compounds by HPLC-FLU

The analysis of pheophytins A and B, and pyropheophytins A and B, and their phorbides was performed by HPLC using fluorescence detection, a method developed based on the work of Hwang et al J. Food Hyg. Soc. Japan Vol. 46, No. 2, 45-48, extended by fluorescence detection at λex 410 nm/λem 666 nm for the A compounds, and λex 436 nm/λem 653 nm for the B compounds.

Sample Preparation

Oil samples were diluted in acetone, 1 g oil in 9 mL acetone, and centrifuged at 14000 rpm for 5 minutes. The clear supernatants were transferred into injection vials, and 10 µl of a sample was injected into the HPLC. As the chlorophyll levels were so low in all practical oil samples, these were not taken into account in the analysis.

Data Analysis

The peak surface areas (in arbitrary units) of the chromatograms indicate the amount of pheophytins, pyropheophytins, pheophorbides and pyropheophorbides present in the oil samples. FIGS. 2 and 3 show the peak surface areas of pheophytins, pyropheophytins, pheophorbides and pyropheophorbides in oil samples after incubation with putative chlorophyllases at pH 5 and pH 7. The sum of the peak surface area of phytines, the sum of peak surface area of phorbides and the peak surface area of the individual compounds are shown. The formation of pheophorbide and pyropheophorbide is a measure for the presence of pheophytinase activity and pyropheophytinase activity, respectively.

Enzymes

Purifine® Phospholipase C (PLC), and Purifine® PI-PLC and a fungal PLA1 were obtained from DSM.

Purifine® Phospholipase C comprises amino acids 38-282 of SEQ ID NO: 2, having the amino acid substitutions 63D, 131S and 134D disclosed in WO2005/086900

Purifine® PI-PLC comprises the mature polypeptide according to SEQ ID NO: 8 disclosed in WO2011/046812.

Fungal PLA1 comprises the mature amino acid sequence of SEQ ID NO: 1 disclosed in European application no. EP18171015.3

Equipment

The overhead mixer was an IKA RW 20 Digital with a flat blade paddle. The centrifuge was a De Laval Gyro—Tester installed with "The Bowl Unit" for continuous separation. The centrifuge bowl was closed with the plug screws installed.

Shear mixing was accomplished with an Ultra-Turrax homogenizer SD-45 with a G450 rotor stator at 10,000 rpm.

Example 1. Expression of a Putative Chlorophyllases in *Pseudomonas*

Putative chlorophyllases (CHL) as provided in the tables of FIGS. 2 and 3 were expressed in the *Pseudomonas* system obtained from Dow Global Technologies Inc. (US20050130160, US20050186666 and US20060110747). The 12 synthetic genes based on the protein sequence of the putative chlorophyllases protein sequences as shown in FIGS. 2 and 3 were designed by optimizing the gene codon usage for *Pseudomonas* according to the algorithm of DNA2.0 (GeneGPS® technology). For cloning purposes, the DNA sequence contain a SpeI site and ribosome binding site (ACTAGTAGGAGGTAACTAATG) (SEQ ID NO: 13) at the 5'-end and a stop codon and XhoI site (TGATGACTCGAG) (SEQ ID NO: 14) at the 3'-end.

SEQ ID NO: 2 shows the codon optimized nucleic acid sequence encoding the putative chlorophyllase SEQ ID NO:1 of *Hordeum vulgare.*

The DNA sequences were inserted in the pDOW1169 vector (Dow Global Technologies Inc., US20080058262)

using SpeI and XhoI restriction enzyme cloning. The pDOW1169 vectors containing the genes encoding the CHL and PPH enzymes under control of a modified lac promotor were then introduced into *Pseudomonas* fluoresce/1s uracil auxotrophic strain DPfl0. The transformed cells were selected after incubating on M9 minimal medium at 30° C. for 48 hours (Dow Global Technologies Inc., US20050186666) without uracil (Schneider et al. 2005).

Correct transformants were pre-cultured in 24 well pre-sterile deep well plates (Axygen, CA, USA) containing 3 ml M9 medium. Plates were covered by a Breathseal (Greiner bio-one, Frickenhausen, Germany) and incubated at 30° C., 550 rpm and 80% humidity for 16 hours in a Microton incubator shaker (Infors AG, Bottmingen, Switzerland). From these cultures 30 μI was used to inoculate a second 24 well pre-sterile deep well plates (Axygen, CA, USA) containing 3 ml M9 medium at 30° C., 550 rpm for 24 hours. After 8 hours, the cultures were induced with IPTG (0.3 mM final concentration). Cultures were harvested by centrifugation for 10 minutes at 2750 rpm and the supernatants removed. The cell pellets were stored overnight at −20° C. The cell pellets from the 3 ml cultures were suspended in 1 ml lysis buffer and incubated for one hour at 37° C. Lysis buffer (1 mM EDTA, 50 mM Tris, pH 8, 0.25 mg/ml lysozyme, 10 mg/ml DnaseI, 25 μM $MgSO_4$ and 0.03% triton). The lysates were centrifuged at 2750 rpm for 10 minutes and the supernatants were removed and stored.

Example 2. Determination of Pyropheophytinase Activity in Cell-Free Extracts in Crude Canola Oil Incubation Crude canola oil from North American origin, high in pheophytins and pyropheophytins was used to determine activity of the enzyme in the supernatant as produced in Example 1 on pyropheophytin A and B in the following way. Buffer (5% (v/v)) was added to oil under high-shear mixing using a Silverson mixer. For pH 5, a 20 mM citric acid buffer was used. For pH 7 a 20 mM phosphate buffer was used. A 24 wells microtiter plate was filled with 1.425 mL buffer-in-oil dispersion per well, and to each well 75 μL, 5% (v/v) cell-free extract (supernatant) produced in Example 1 was added. A list of tested samples is given in the tables of FIG. 2 and FIG. 3, and include a positive reference containing *Chlamydomonas reinhardtii* pyropheophytinase and negative control Green Fluorescent Protein (GFP). The microtiter plate was covered with plastic foil [Fasson S695]. Each well was stirred with an individual magnetic stirring bar. Incubations were performed at 50° C. using a KBMD microtiter-plate stirrer. Samples were taken after 24 hours and analysed for the presence of pheophytins A and B, and pyropheophytins A and B, and their phorbides using HPLC-FLU as described above.

The results in FIGS. 2 and 3 show that only CHL26, a putative chlorophyllase from *Hordeum vulgare*, was able to hydrolyse all pheophytins and pyropheophytins into their respective (pyro)pheophorbides at pH 7 and pH 5.

Example 3. Incubation of Crude Canola Oil with CHL26 Versus Time

Incubation of crude canola oil with 5% cell free extract of *Hordeum vulgare* putative chlorophyllase CHL26 produced as described in Example 1, was repeated in the same way as described in Example 2 at pH7. Samples were taken after 30 min, 2 hr, 5 hr, and 24 hr. Pyropheophytin a and b, and pheophytin a and b, pyropheophorbide a and b and pheophorbide a and b were measured by HPLC as described above.

The formation of the reaction products pyropheophorbide a and b and pheophorbide a and b in Table 1 is expressed as percentage of the amount reaction product (respective phorbide molecule) after 24 hr.

Table 2 shows the relative amounts of pheophytins and pyropheophytins as a function of time after 0.5, 2 and 5 hr, expressed in percentages relatively to the value at t=0 (average of 4 measurements).

TABLE 1

Relative HPLC results for all reaction products after incubation for 0.5, 2, 5 and 24 hours at pH 7 and 50° C., in percentages relative to value after 24 hrs.

| Time [hr] | Pheophorbide B (%) | Pyropheophorbide B (%) | Pheophorbide A (%) | Pyropheophorbide A (%) |
|---|---|---|---|---|
| 0.5 | 53.7 | 48.8 | 69.4 | 56.7 |
| 2 | 85.3 | 95.5 | 96.4 | 90.0 |
| 5 | 92.9 | 92.9 | 98.7 | 94.3 |
| 24 | 100.0 | 100.0 | 100.0 | 100.0 |

TABLE 2

Relative HPLC results for all phytin compounds after incubation for 0.5, 2, and 5 hours at pH 7 and 50° C., in percentages relative to value at t = 0.

| Time [hr] | Pheophytin B (%) | Pyropheophytin B (%) | Pheophytin A (%) | Pyropheophytin A (%) | Sum phytins (%) |
|---|---|---|---|---|---|
| 0 | 100.0 | 100.0 | 100.0 | 100.0 | 100.0 |
| 0.5 | 34.7 | 43.8 | 34.4 | 46.4 | 41.4 |
| 2 | 0.0 | 12.7 | 0.0 | 12.9 | 8.2 |
| 5 | 0.0 | 6.2 | 0.0 | 6.0 | 3.9 |

The results in Table 1 and 2 show that enzyme CHL26 from *Hordeum vulgare* is able to hydrolyse both pheophytin and pyropheophytin, and both the a and b compounds. After 2 hrs all pheophytins were converted (below detection limit), whereas after 5 hours almost all the pyropheophytins were converted.

Example 4. Production of CHL26 and ELDC94 by 10 L Bioreactor Fermentation

Strains and Inoculum

Of a *P. fluorescens* strain containing CHL26 (SEQ ID NO: 1) and *Chlamydomonas reinhardtii* (ELDC94; SEQ ID NO: 12) chlorophyllase as described in Example 1 a pre-culture was prepared in one-phase shake flasks with complex medium comprising yeast extract, slats and glycerol as a C-source, which was used as inoculum for the 10 L fermentations with inoculation ratio of 10% described below.

10 L Fermentations

Fermentation process was based on industrial *Pseudomonas fluorescens* fermentations (fed-batch process, sugar limited, IPTG induced). The fermentation process consisted of biomass production under exponential feed of glucose as C-source followed by production phase under IPTG induction system. After 23 hr fermentation (end of biomass production phase), IPTG was added to a final concentration of 0.125 mM in order to induce enzyme production. The feed rate of C-source (glucose) was reduced to ~70% of maximum and fermentation prolonged till 48-55 hours after inoculation.

At the end of fermentation, the broth was killed off and the enzyme release via benzoate treatment followed by pH increase of the fermentation broth.

Recovery

The intra-cellular enzyme was released by homogenization. Two passes at 750 bars, with a cooling period of 12-hours in-between was applied. Subsequently the homogenized broth was diluted with 30% water, 15% DBF (Dicalite BF), Calcium Chloride (20 g/kg original broth), and Flocculent C577 (0.1% on original broth) were added. The pH was adjusted to 8, and the material was clarified and ultra-filtrated. The UF was stabilized with 50% glycerol, and to ensure full killing of remaining bacteria MEP (methyl/ethyl paraben in a solution with propene-diol) was added, diluting the product with about 15% v/v.

Activity

Activity on p-NP Substrates

The enzyme activity was determined using the chromogenic substrate 4-nitrophenyl butyrate (Sigma N9874). Substrate stock solution: 50 mM pNP-butyrate in acetonitrile. Substrate solution: Prior to use the substrate stock solution was mixed in ratio 1:4 with 0.1 M phosphate buffer pH 7.0 also containing 0.2% BSA and 2.0% Triton X-100.

In micro titer plates, 120 μL phosphate buffer (same as above) was mixed with 15 μL substrate solution and equilibrated at 37° C. After starting the reaction by adding 15 sample, the OD at 405 nm was measured for 5 minutes. Also, a blank measurement was done by adding 15 μL buffer instead of sample. The slope of the linear part of the curve is used as measure for the activity. Samples were diluted such to assure that the absorbance increase after 5 minutes is less than 1.0.

Activity is calculated as follows:

$$U/mL=(\Delta Abs/\min\ sample-\Delta Abs/\min\ blank)/(\varepsilon_{pNP}\times 5)\times 1000\times 150/15\times Df/W$$

$\varepsilon_{pNp}$=Molar Extinction Coefficient of para-nitro-phenol [L·mol-1·cm-1]

5=Incubation time [min]

1000=factor from mmol to μmol

150=assay volume [μL]

15=sample volume [μL]

Df=Dilution factor

W=weight of sample (g)

The activity is expressed as the amount of enzyme that liberates 1 micromol p-nitrophenol per minute under the conditions of the test. Calibration is done using a 4-nitrophenol standard solution (Sigma N7660) diluted in the above-mentioned phosphate buffer.

The activity of the final formulations of CHL26 was 1.4 U/g (0.5 w/w %), and of ELDC94 87 U/g (0.04 w/w %).

Example 5. Incubation of Crude Canola Oil with an Enzyme Having Pyropheophytinase Activity Derived from *Hordeum vulgare* (CHL26) Compared to Incubation of Crude Canola Oil with a Reference Enzyme (ELDC94) from *Chlamydomonas reinhardtii* at Various Conditions Crude canola oil was incubated with 0.5 w/w % cell free extract of *Hordeum vulgare* putative chlorophyllase CHL26 and compared to 0.04 w/w % of cell-free extract of *Chlamydomonas reinhardtii* chlorophyllase (coded ELDC94=Ref) both enzymes produced as described in Example 4. The incubation was performed on 10 g scale (10 g oil in 15 ml glass reaction vessels incubated on a hot plate aluminium reaction block with temperature control. Contents are kept vigorously stirred by magnetic bars), and now at three different temperatures (40, 50 and 60° C.), and under four regimes with varying acidity of the aqueous phase:

Acidic: 400 ppm citric acid pre-treatment;

Mildly acidic: pre-treatment with 500 ppm citric acid and 138 ppm caustic (NaOH);

Neutral: only water;

Mildly alkaline: pre-treatment with 150 ppm NaOH.

The total water level during incubation is 3% w/w, which includes enzyme formulation and pre-treatment solutions. Prior to the experiment, the acidity of the aqueous environment was assessed by diluting the pre-treated oil 1:1 with water and then the pH was measured by a pH meter. This resulted in the following pH values, indicative for the acidity of the aqueous environment in the dispersion during reaction: Acidic: pH 3.4; mildly acidic: pH 4.5; Neutral: pH 5.9 and alkalic pH 7.9.

For pre-treatment with citric acid, the citric acid (as 50% w/w solution) was added to the oil at 70° C., kept stirred at 70° C. for 30 minutes, subsequently the temperature was reduced to incubation temperature and for the mildly acid condition the NaOH (as 2.0% w/w solution) was added. In case of only NaOH addition, the oil was stirred at incubation temperature for 30 minutes.

During incubation, samples were taken after 0.5, 2, 4 and 24 hours, and analysed by HPLC-Flu as described in Example 2, now against a set of standards with known concentration. Concentrations of all substrates (chlorophyll, pheophytins, pyropheophytin—a and b) and all reaction products (chlorophyllide, pheophorbide, pyropheophorbide—a and b) were summed into total substrates and total reaction products, respectively, in mg/kg oil. All results are given in percentage of substrates and reaction products in the table below.

The results in Tables 3, 4 and 5 show that the *Hordeum vulgare* enzyme CHL26 according to SEQ ID NO: 1 has a wider application range in the presence of acid and caustic and is active at a higher temperature than the reference chlorophyllase from *Chlamydomonas reinhardtii*.

TABLE 3

Chlorophyll derivatives (wt %) in crude canola oil after incubation with the CHL26 enzyme from *Hordeum vulgare* or the reference enzyme ELDC94 from *Chlamydomonas reinhardtii* at different conditions at 40° C.

| | | CHL26 | | Reference | |
|---|---|---|---|---|---|
| 40° C. Condition | Time [hr] | Sum substrates | Sum reaction products | Sum substrates | Sum reaction products |
| — | 0 | 94.9 | 5.1 | 94.9 | 5.1 |
| Acidic | 0.5 | 66.5 | 33.5 | 80.6 | 19.4 |
| | 2 | 56.4 | 43.6 | 78.1 | 21.9 |
| | 4 | 51.9 | 48.1 | 75.2 | 24.8 |
| | 24 | 45.4 | 54.6 | 75.2 | 24.8 |
| Mildly acidic | 0.5 | 29.1 | 70.9 | 35.2 | 64.8 |
| | 2 | 10.0 | 90.0 | 28.7 | 71.3 |
| | 4 | 3.4 | 96.6 | 19.0 | 81.0 |
| | 24 | 0.0 | 100.0 | 15.4 | 84.6 |
| Neutral | 0.5 | 30.9 | 69.1 | 3.2 | 96.8 |
| | 2 | 10.0 | 90.0 | 1.7 | 98.3 |
| | 4 | 4.4 | 95.6 | 1.8 | 98.2 |
| | 24 | 3.0 | 97.0 | 1.7 | 98.3 |
| Mildly alkaline | 0.5 | 71.8 | 28.2 | 60.7 | 39.3 |
| | 2 | 72.5 | 27.5 | 55.2 | 44.8 |
| | 4 | 57.4 | 42.6 | 38.2 | 61.8 |
| | 24 | 14.8 | 85.2 | 32.8 | 67.2 |

TABLE 4

Chlorophyll derivatives (wt %) in crude canola oil after incubation with the CHL26 enzyme from *Hordeum vulgare* or the reference enzyme ELDC94 from *Chlamydomonas reinhardtii* at different conditions at 50° C.

| | | CHL26 | | Reference | |
|---|---|---|---|---|---|
| 50° C. Condition | Time [hr] | Sum substrates | Sum reaction products | Sum substrates | Sum reaction products |
| — | 0 | 94.9 | 5.1 | 94.9 | 5.1 |
| Acidic | 0.5 | 87.7 | 12.3 | 89.9 | 10.1 |
| | 2 | 87.7 | 12.3 | 92.6 | 7.4 |
| | 4 | 88.5 | 11.5 | 93.4 | 6.6 |
| | 24 | 88.0 | 12.0 | 92.6 | 7.4 |
| Mildly acidic | 0.5 | 27.5 | 72.5 | 21.3 | 78.7 |
| | 2 | 9.7 | 90.3 | 11.7 | 88.3 |
| | 4 | 2.7 | 97.3 | 8.7 | 91.3 |
| | 24 | 2.2 | 97.8 | 2.1 | 97.9 |
| Neutral | 0.5 | 28.5 | 71.5 | 5.8 | 94.2 |
| | 2 | 13.7 | 86.3 | 3.9 | 96.1 |
| | 4 | 5.5 | 94.5 | 2.0 | 98.0 |
| | 24 | 0.6 | 99.4 | 0.6 | 99.4 |
| Mildly alkaline | 0.5 | 66.8 | 33.2 | 54.6 | 45.4 |
| | 2 | 66.4 | 33.6 | 62.1 | 37.9 |
| | 4 | 51.1 | 48.9 | 51.8 | 48.2 |
| | 24 | 10.9 | 89.1 | 41.0 | 59.0 |

TABLE 5

Chlorophyll derivatives (wt %) in crude canola oil after incubation with the CHL26 enzyme from *Hordeum vulgare* or the reference enzyme ELDC94 from *Chlamydomonas reinhardtii* at different conditions at 60° C.

| | | CHL26 | | Reference | |
|---|---|---|---|---|---|
| 60° C. Condition | Time [hr] | Sum substrates | Sum reaction products | Sum substrates | Sum reaction products |
| — | 0 | 94.9 | 5.1 | 94.9 | 5.1 |
| Acidic | 0.5 | 90.5 | 9.5 | 94.7 | 5.3 |
| | 2 | 90.5 | 9.5 | 95.0 | 5.0 |
| | 4 | 90.7 | 9.3 | 92.7 | 7.3 |
| | 24 | 90.5 | 9.5 | 94.9 | 5.1 |

TABLE 5-continued

Chlorophyll derivatives (wt %) in crude canola oil after incubation with the CHL26 enzyme from *Hordeum vulgare* or the reference enzyme ELDC94 from *Chlamydomonas reinhardtii* at different conditions at 60° C.

| | | CHL26 | | Reference | |
|---|---|---|---|---|---|
| 60° C. Condition | Time [hr] | Sum substrates | Sum reaction products | Sum substrates | Sum reaction products |
| Mildly acidic | 0.5 | 13.5 | 86.5 | 60.4 | 39.6 |
| | 2 | 2.5 | 97.5 | 65.7 | 34.3 |
| | 4 | 4.1 | 95.9 | 66.4 | 33.6 |
| | 24 | 2.0 | 98.0 | 68.5 | 31.5 |
| Neutral | 0.5 | 29.0 | 71.0 | 11.9 | 88.1 |
| | 2 | 10.1 | 89.9 | 7.4 | 92.6 |
| | 4 | 5.2 | 94.8 | 4.6 | 95.4 |
| | 24 | 0.0 | 100.0 | 1.5 | 98.5 |
| Mildly alkaline | 0.5 | 57.7 | 42.3 | 52.5 | 47.5 |
| | 2 | 65.1 | 34.9 | 80.4 | 19.6 |
| | 4 | 67.4 | 32.6 | 80.4 | 19.6 |
| | 24 | 33.0 | 67.0 | 93.0 | 7.0 |

Example 6. Incubation of Solvent Extracted Crude Canola Oil with an Enzyme Having Pyropheophytinase Activity Derived from *Hordeum vulgare* (CHL26) Compared to a Reference Enzyme from *Chlamydomonas reinhardtii* (ELDC94)

A 35-pound container of solvent extracted crude canola oil was poured into large stainless-steel container and made uniform with IKA mixer.

After mixing, approximately 1.5 kg of crude canola was placed into a 2 liter jacketed glass beaker with an overhead mixer with a square paddle and mixed at 90 revolutions per minute (rpm). The jacket temperature was set at 65° C. 0.7 grams of enzyme ELDC94 (reaction 1) or 7.5 grams of CHL26 (reaction 2), produced as described in Example 4, were added to the oil together with 100 grams of deionized water once the oil temperature had reached the set point. The material was shear mixed for 1 minute while covered with plastic wrap. The jacketed glass beaker was moved back to the overhead mixer and covered with plastic wrap. The materials were incubated with the enzymes for 24 hours at 250 rpm.

1.5 grams of 50% (wt. %) citric acid was added to the mixing oil. The set point of the jacket was reduced to 55° C. Once the material reached 55° C., the oil was moved to the shear mixer. 1.2 mL of 4 N NaOH was added to the oil and shear mixed 30 seconds. 0.3 grams of Purifine® Phospholipase C (PLC) and 30 grams of deionized water were added. The oil was shear mixed for 1 minute while covered with plastic wrap. The jacketed glass beaker was moved back to the overhead mixer and covered again with plastic wrap. The oil was mixed for 2 hours at 55° C. at 250 rpm.

The beaker was moved back to the high shear mixer and 0.1 grams of a fungal phospholipase $A_1$ ($PLA_1$) enzyme was added to the oil and shear mixed 1 minute while covered with plastic wrap. The jacketed glass beaker was moved back to the overhead mixer and covered again with plastic wrap. The oil was mixed for 2 hours at 55° C. at 250 rpm. Increased the set point of the water bath to 75° C. Once the oil reached 75° C., the oil was centrifuged utilizing a Gyro-Centrifuge with the bowl with holes closed. Samples of the oil and gums were collected and analysed for the presence of P, Ca, Mg and Fe and chlorophyll derivatives (using HPLC) as described above.

The mixture of oil and heavy phase remaining in the centrifuge bowl were poured in to a 400 mL beaker where the oil was decanted off. The remaining oil and heavy phase were placed into 50 mL centrifuge tubes and spun. The oil from the decanted bowl and in the tubes was discarded and liquid heavy phases were combined.

The results in Table 6 and FIG. 4 *a*) show that the CHL26 enzyme having pyropheophytinase activity according SEQ ID NO: 1 is able to reduce chlorophyll derivatives in solvent extracted crude canola oil. Chlorophyll substrates are chlorophyll, pheophytin, and pyropheophytin and chlorophyll products are chlorophyllide, pheophorbide and pyropheophorbide.

TABLE 6

Compounds (in ppm) in crude canola oil after treatment with enzymes CHL26 and the reference enzyme ELDC94

| | | | | | Chlorophyll derivatives (HPLC) (ppm) | | |
|---|---|---|---|---|---|---|---|
| Enzyme | P | Ca | Mg | Fe | Total | Substrates | Products |
| None* | 903.0 | 243.0 | 127 | 9.89 | 15.40 | 14.72 | 0.50 |
| ELDC94 | 88.5 | 80.9 | 14.6 | 1.49 | 8.39 | 0.21 | 8.18 |
| CHL26 | 82.0 | 77.3 | 14.1 | 1.58 | 9.15 | 1.26 | 7.89 |

*Starting material (crude canola oil)

The results in FIG. 4 *b*) show that there are still unreacted phospholipids present in the collected heavy phase, which is an indication that the phospholipase reactions were too short to come to completion.

Example 7. Incubation of Pressed Crude Canola Oil with the CHL26 Enzyme at Varying Conditions A 35-pound container of pressed crude canola oil was poured into large stainless-steel container and made uniform with IKA mixer Reaction 3—CHL26 Incubation with PLC and PI-PLC at pH 4.5 for 2 hr, Followed by a 2 hr Incubation with PLA1

About 1.5 kg of crude canola was placed into a 2 liter jacket glass beaker with an overhead mixer with a square paddle. The oil was mixed at 90 rpm. The jacket temperature was set at 70° C. 1.5 grams of 50% (wt. %) citric acid was added to the mixing oil and shear mixed 1 minute. The set point of the jacket was reduced to 60° C. Once the material reached 60° C., the oil was moved to the shear mixer. 1.2 mL of 4 N NaOH was added to the oil and shear mixed 30 seconds. 0.3 grams of Purifine PLC (LR79.14 Feb. 2018), 0.02 grams of Purifine PI-PLC, 7.5 grams of CHL26 enzyme [*Hordeum vulgare* var. *distichum* (barley, plant)], produced as described in Example 4, and 100 grams of deionized water. The material was shear mixed for 1 minute while covered with plastic wrap. The jacketed glass beaker was moved back to the overhead mixer and covered again with plastic wrap. The oil was mixed for 2 hours at 60° C. at 250 rpm.

The jacketed glass beaker was again moved to the hear mixer where 0.075 grams of $PLA_1$ (notebook, 0743B2) was added and the oil was shear mixed 1 minute. The jacketed glass beaker was moved back to the overhead and covered with plastic wrap. The oil was mixed and the reactions were allowed to continue for 2 hours at 250 rpm. Increased the set point of the water bath to 75° C. Once the oil reached 75° C., the oil was centrifuged utilizing Gyro-Centrifuge with the bowl with holes closed. Samples of the oil and gums were collected.

The mixture of oil and heavy phase remaining in the centrifuge bowl were poured in to a 400 mL beaker where the oil was decanted off. The remaining oil and heavy phase were placed into 50 mL centrifuge tubes and spun. The oil from the decanted bowl and in the tubes was discarded and liquid heavy phases were combined.

Reaction 4—ELDC94 Incubation with PLC and PI-PLC at pH 4.5 for 2 hr, Followed by a 2 hr Incubation with $PLA_1$ The same procedure from reaction 1 above was employed for enzyme ELDC94, using 0.61 grams of the formulated enzyme solution (produced as described in Example 4).

Reaction 5—CHL26 Incubation with PLC and PI-PLC at pH 4.5 for 2 hr, Followed by a 4 hr Incubation with $PLA_1$ The same procedure was followed as reaction 1, but the PLA1 reaction was allowed to react for 4 hours instead of only 2 hours.

Reaction 6—CHL26 Incubation with PLC and PI-PLC at pH 4.5 for 2 hr, Followed by a 4 hr Incubation with $PLA_1$ The same procedure was followed as reaction 3, except twice the amount of CHL26 (15 grams total) was added to the reaction.

Reaction 7—CHL26 Incubation with PLC and PI-PLC at Neutral pH for 2 hr, Followed by a 4 hr Incubation with $PLA_1$ The same procedure was followed as reaction 1, except no pH adjustment was made.

Reaction 8—SBO CHL26 Incubation with PLC and PI-PLC at pH 4.5 for 2 hr, Followed by a 2 hr Incubation with $PLA_1$ The same procedure as reaction 1, but the oil was a solvent extracted crude soybean oil (SBO).

In Table 7 the phosphorus (P) and FIG. 5*b*), calcium (Ca), magnesium (Mg), and iron (Fe) contents of the oils and the respective gums before and after enzyme treatments according to reactions 1 to 6 are shown. At neutral pH, a higher amount of P remained in the oil as compared to reaction at pH 4.5.

The results in Table 8 and FIG. 5*a*) show that the CHL26 enzyme converts a higher amount of chlorophyll derivatives in crude canola oil as compared to ELDC94, when the enzymes are incubated under the same conditions (reactions 1 and 2).

In the present example the CHL26 enzyme converted a higher amount of chlorophyll substrates into the respective chlorophyll products in crude canola oil under neutral conditions as compared to acid conditions (pH 4.5) (compare reaction 7 with reactions 3, 5 and 6).

The CHL26 enzymes also converts chlorophyll substrates in soybean oil into the respective chlorophyll products (reaction 8).

The results in Table 8 also show that a higher amount of chlorophyll products were found in the gums (heavy phase) when the oil was reacted with the CHL26 enzyme as compared to the reaction with the ELDC94 enzyme.

TABLE 7

Compounds in canola oil (Can) or soybean oil (SBO) after treatment with the CHL26 enzyme compared to reference enzyme ELDC94 and/or no enzyme treatment

| Reaction | Oil | pH | P | Ca (ppm) | Mg | Fe |
|---|---|---|---|---|---|---|
| None, Crude | Can | — | 210 | 90.5 | 36.7 | 0.90 |
| Rxn 3 - CHL26 | Can | 4.5 | 10.7 | 7.9 | 1.7 | 0.20 |
| Rxn 4 - ELDC94 | Can | 4.5 | 4.4 | 3.3 | 0.9 | 0.07 |

TABLE 7-continued

Compounds in canola oil (Can) or soybean oil (SBO) after treatment with the CHL26 enzyme compared to reference enzyme ELDC94 and/or no enzyme treatment

| Reaction | Oil | pH | P | Ca | Mg | Fe |
|---|---|---|---|---|---|---|
| | | | | (ppm) | | |
| None, Crude | Can | — | 210 | 90.5 | 36.7 | 0.90 |
| Rxn 5 - CHL26 | Can | 4.5 | 3.9 | 2.8 | 0.6 | 0.16 |
| Rxn 6 - CHL26 | Can | 4.5 | 2.0 | 1.5 | 0.4 | 0.10 |
| Rxn 7- CHL26 | Can | Neutral | 103 | 80.9 | 10.5 | 0.88 |
| None, Crude | SBO | — | 773 | 66.2 | 64.3 | 0.76 |
| Rxn 8 - CHL26 | SBO | 4.5 | 5.8 | 0.5 | 0.7 | 0.04 |

TABLE 8

Chlorophyll derivatives in canola oil or soybean oil and the separated gums after treatment with the CHL26 enzyme compared to reference enzyme ELDC94 and/or no enzyme treatment

| | Chlorophyll derivatives in the oil (ppm) | | Chlorophyll derivatives in the gums (ppm) | |
|---|---|---|---|---|
| Oil | Substrates | Products | Substrates | Products |
| Crude Canola | 13.13 | 0.90 | — | — |
| Rxn 3 - CHL26, pH 4.5 | 4.19 | 7.97 | 0.06 | 6.39 |
| Rxn 4 - ELDC94, pH 4.5 | 10.28 | 2.62 | 0.18 | 3.06 |
| Crude Canola | 13.13 | 0.90 | — | — |
| Rxn 5, CHL26, pH 4.5 | 6.85 | 5.69 | 0.30 | 2.68 |
| Rxn 6 - CHL 26, pH 4.5 | 6.01 | 6.41 | 0.19 | 1.99 |
| Rxn 7 - CHL26, neutral pH | 1.26 | 10.02 | b.d. | 5.02 |
| Crude SBO | 0.31 | b.d. | — | — |
| Rxn 8 - CHL26, pH 4.5 | 0.28 | b.d. | b.d. | 0.56 |

b.d.—below detection,

Example 8. Use of CHL26 Enzyme in Caustic Refining Application of Canola Oil and Soybean Oil The following experiments are an evaluation of the CHL26 in a caustic refining application where the oil has been treated with a phosphoric acid and sodium hydroxide, as occurs in industrial processes of canola and soybean oils. A "once refined" product is an oil that was treated with phosphoric acid, then treated with sodium hydroxide to convert the Free Fatty Acids (FFA) into sodium soaps that are water soluble and removed in water or "heavy" phase of the "refining" centrifuge. The oil was then washed with water (2 to 10 percent w/w) to remove the remaining soaps and residual phospholipids present in the oil. Optionally, the enzymes were evaluated after the refining centrifuge in the water washing step, but at a much lower temperature.

A five-gallon plastic pail of Once Refined Canola (ORCAN) oil was mixed with a high shear mixer to make uniform. 2-3 kg samples were pulled for use in the experiments below.

Reaction 9—ELDC94-Comparative 2 kg of once refined canola was placed into a 4 liter glass beaker on a hot plate with overhead mixing at 90 rpm. The oil was heated to 60° C. under agitation. Once the material reached 60° C., the beaker was moved to the shear mixer. 0.8 grams of enzyme ELDC94 (produced as described in Example 4) and 100 grams of deionized water were added to the oil. The material was shear mixed for 1 minute while covered with plastic wrap to minimize water loss. The glass beaker was moved back to the overhead mixer and covered with plastic wrap. The oil was mixed for 4 hours at 60° C. at 250 rpm. The temperature was increased to 75° C. The oil was centrifuged utilizing Gyro-Centrifuge. The separated oil was collected.

The mixture of oil and heavy phase remaining in the centrifuge bowl were poured in to a 400 mL beaker where the oil was decanted off. The remaining oil and heavy phase were placed into 50 mL centrifuge tubes and spun. The oil from the decanted bowl and in the tubes was discarded and liquid heavy phases were combined. The heavy phase was a dark green.

Reaction 10— ELDC94-Comparative

Reaction 10 was a repeat of reaction 9, except 3 kg of oil was used and 2.0 grams of ELDC94 (produced as described in Example 4).

After the analyses of the oils from reaction 9 and 10, the oils were combined mixed and analysed again.

Reaction 11—CHL26

Reaction 11 was a repeat of reaction 9, except that 10.1 grams of CHL26 (produced as described in Example 4) was used instead of ELDC94. The heavy phase was a lighter green than reactions 9 and 10.

Reaction 12—CHL26

Reaction 12 was a repeat of reaction 10, except that 20 grams of CHL26 was utilized.

After analyses, the oils of reaction 11 and 12 were combined and mixed and after mixing analysed again.

Reaction 13—ELDC94-Comparative 3 kg of once refined soybean oil (ORSBO) was pulled from a caustic refining production line number 1 after the water washing centrifuge. The oil was placed into a 4 liter glass beaker and placed onto a hot plate with overhead mixing with a square mixing paddle (90 rpm). Once the material cooled 60° C., the beaker was moved to a shear mixer. 1.0 grams of ELDC94 enzyme produced as described in Example 4) and 150 grams of deionized water were added to the oil. The material was shear mixed for 1 minute while covered with a plastic wrap to minimize moisture loss. The glass beaker was moved back to the overhead mixer and again covered with a plastic wrap. The oil was mixed for 4 hours at 60° C. at 250 rpm. The temperature was increased to 75° C. and then the oil was centrifuged utilizing Gyro-Centrifuge.

Collected oil and heavy samples for further analyses.

The remaining oil and heavy phase remaining in the centrifuge bowl were poured in to a 400 mL beaker where the oil was decanted off. The remaining oil and heavy phase were placed into 50 mL centrifuge tubes and spun. The remaining oil in the tubes was discarded and liquid heavy phases were combined. The heavy phase was colorless, no discernible color pigments.

Reaction 14—CHL26

Reaction 14 was a repeat of reaction 13, except that 15 grams of CHL26 (produced as described in Example 4) was utilized instead of ELDC94.

Reaction 15—EDLC94-Comparative 3 kg grams of once refined soybean oil (ORSBO) was pulled from a caustic refining production line number 1 after the water washing centrifuge. The oil was placed into a 4 liter glass beaker and placed onto a hot plate with overhead mixing with a square mixing paddle (90 rpm). Once the material cooled 60° C., the beaker was moved to a shear mixer. 1.2 grams of ELDC94 enzyme produced as described in Example 4 and 150 grams of deionized water were added to the oil. The material was shear mixed for 1 minute while covered with a plastic wrap to minimize moisture loss. The glass beaker was moved back to the overhead mixer and again covered with a plastic wrap. The oil was mixed for 4 hours at 60° C. at 250 rpm. The temperature was increased to 75° C. and then the oil was centrifuged utilizing Gyro-Centrifuge.

Collected oil and heavy phase (gums) samples for further analyses.

The remaining oil and heavy phase remaining in the centrifuge bowl were poured in to a 400 mL beaker where the oil was decanted off. The remaining oil and heavy phase were placed into 50 mL centrifuge tubes and spun. The remaining oil in the tubes was discarded and liquid heavy phases were combined. The heavy phase was colorless, no discernible color pigments.

Reaction 16—CHL26

Reaction 16 was a repeat of reaction 15, except that 15 grams of CHL26 was utilized.

The results of reactions 9 to 16 and the results of the combined and mixed oils from reaction 9 and 10 and from reactions 11 and 12 are shown in Table 9 and FIG. 6.

The results in Table 9 and FIG. 6 show that the enzyme CHL26, having pyropheophytinase converts a higher amount of chlorophyll substrates (chlorophyll, pheophytin and pyropheophytin) to its chlorophyll products (chlorophyllide, pheophorbide, pyropheophorbide) than the reference chlorophyllase enzyme ELDC94.

TABLE 9

Chlorophyll derivatives (substrates and products) in once refined canola oil (ORCAN) and once refined soybean oil (ORSBO) after caustic refining and after treatment with the CHL26 enzyme and the ELDC94 (reference) enzyme

| Enzyme reaction | Chlorophyll derivatives in oil (ppm) Substrates | Products |
|---|---|---|
| None: ORCAN | 27.38 | b.d. |
| Rxn 9 - ELDC94 | 7.87 | 4.99 |
| Rxn 10 - ELDC94 | 19.37 | 0.42 |
| Combined 9 & 10 | 18.71 | 0.39 |
| Rxn 11 - CHL26 | 11.60 | 4.96 |
| Rxn 12 - CHL26 | n.m. | n.m. |
| Combined 11 & 12 | 12.00 | 6.19 |
| None: ORSBO | 3.85 | b.d. |
| Rxn 13 - ELDC94 | 1.09 | 0.06 |
| None: ORSBO | 3.90 | b.d. |
| Rxn 14 - CHL26 | 1.12 | 0.18 |
| None: ORSBO | 3.90 | b.d. |
| Rxn 15 - ELDC94 | 2.05 | b.d. |
| Rxn 16 - CHL26 | 1.77 | 0.07 |

b.d. = below detection
n.m. = not measured

The results of Table 10 show the contents of free fatty acids (FFA), soap and phosphor and Ca, Mg in once refined canola oil and once refined soybean oil after enzymatic treatments described above.

TABLE 10

Composition of once refined canola oil (ORCAN), once refined soybean (ORSBO) oil after caustic refining and after treatment with the CHL26 enzyme and the ELDC94 (reference) enzyme

| | FFA (%) | Soap (ppm) | P (ppm) | Ca (ppm) | Mg (ppm) | Fe (ppm) |
|---|---|---|---|---|---|---|
| ORCAN | 0.05 | 195 | 4.5 | 0.9 | 0.2 | 0.03 |
| Rxn 9 - ELDC94 | 0.05 | b.d. | 0.5 | 0.7 | tr | 0.02 |
| Rxn 10 - ELDC94 | 0.07 | b.d. | 0.6 | 1.8 | tr | 0.03 |
| Combined 9 & 10 | 0.06 | b.d. | 0.6 | 0.7 | tr | 0.07 |
| Rxn 11 - CHL26 | 0.06 | tr | 1.6 | 2.4 | 0.1 | 0.11 |
| Rxn 12 - CHL26 | 0.06 | b.d. | 1.7 | 2.9 | 0.1 | 0.07 |
| Combined 11 & 12 | 0.06 | tr | 1.7 | 2.7 | 0.1 | 0.09 |
| ORSBO | 0.12 | 20 | 0.3 | 0.2 | b.d. | b.d. |
| Rxn 13 - ELDC94 | 0.10 | b.d. | 0.2 | 0.1 | b.d. | b.d. |
| ORSBO | 0.06 | 27 | 1.0 | 0.4 | tr | b.d. |
| Rxn 14 - CHL26 | 0.05 | b.d. | 0.2 | 0.1 | b.d. | b.d. |
| ORSBO | 0.03 | 242 | 2.8 | 0.7 | 0.2 | tr |
| Rxn 15 - ELDC94 | 0.02 | tr | 0.3 | 0.2 | b.d. | 0.1 |
| ORSBO | 0.05 | 396 | 3.3 | 0.9 | 0.2 | b.d. |
| Rxn 16 - CHL26 | 0.03 | tr | b.d. | 0.2 | b.d. | b.d. |

tr = trace
b.d. = below detection
n.m. = not measured

What is claimed is:

1. A process for treating an oil comprising a chlorophyll substrate, the process comprising contacting the oil with a polypeptide having decolorase activity or a composition comprising the polypeptide, wherein the polypeptide is dosed into the oil in an amount of 1 to 50 U/gram oil, wherein the treatment reduces the total concentration of chlorophyll substrates in the oil by at least 5% by weight, compared to the total concentration of chlorophyll substrates in the oil prior to treatment.

2. The process of claim 1, wherein the polypeptide has chlorophyllase activity, pheophytinase activity, pyropheophytinase activity, or combinations thereof.

3. The process of claim 1, wherein the oil comprises a triacylglycerol-based oil selected from the group consisting of canola oil, castor oil, coconut oil, coriander oil, corn oil, cottonseed oil, hazelnut oil, hempseed oil, linseed oil, mango kernel oil, meadowfoam oil, neat'sfoot oil, olive oil, palm oil, palm kernel oil, palm olein, peanut oil, rapeseed oil, rice bran oil, safflower oil, sasanqua oil, sesame oil, soybean oil, sunflower seed oil, tall oil, tsubaki oil, vegetable oil, and an oil from algae.

4. The process of claim 1, wherein the oil comprises an oil from algae.

5. The process of claim 1, wherein the oil comprises an oil selected from the group consisting of a crude non-degummed oil, a degummed oil, a caustic refined oil, a caustic refined and water washed oil, or a water degummed oil.

6. The process of claim 1, wherein the treatment reduces the total concentration of chlorophyll substrates in the oil by at least 50% by weight, compared to the total concentration of chlorophyll substrates in the oil prior to treatment.

7. The process of claim 1, wherein the chlorophyll substrate comprises pyropheophytin, and at least a portion of the pyropheophytin is converted into pyropheophorbide.

8. The process of claim 7, wherein the treatment reduces the concentration of pyropheophytin in the oil by at least 5% by weight, compared to the total concentration of pyropheophytin in the oil prior to treatment.

9. The process of claim 8, wherein the treatment reduces the concentration of pyropheophytin in the oil by at least 50% by weight, compared to the total concentration of pyropheophytin in the oil prior to treatment.

10. The process of claim 1, wherein the chlorophyll substrate comprises pheophytin, and at least a portion of the pheophytin is converted into pheophorbide.

11. The process of claim 10, wherein the treatment reduces the concentration of pheophytin in the oil by at least 5% by weight, compared to the total concentration of pheophytin in the oil prior to treatment.

12. The process of claim 11, wherein the treatment reduces the concentration of pheophytin in the oil by at least 50% by weight, compared to the total concentration of pheophytin in the oil prior to treatment.

13. The process of claim 1, wherein the chlorophyll substrate comprises chlorophyll, and at least a portion of the chlorophyll is converted into chlorophyllide.

14. The process of claim 13, wherein the treatment reduces the concentration of chlorophyll in the oil by at least 5% by weight, compared to the total concentration of chlorophyll in the oil prior to treatment.

15. The process of claim 14, wherein the treatment reduces the concentration of chlorophyll in the oil by at least 50% by weight, compared to the total concentration of chlorophyll in the oil prior to treatment.

16. The process of claim 1, wherein the polypeptide is contacted with the oil at a pH of from 2 to 10.

17. The process of claim 16, wherein the polypeptide is contacted with the oil at a pH of from 4.0 to 5.0.

18. The process of claim 1, wherein the polypeptide is contacted with the oil for from 1.5 hours to 6 hours.

19. The process of claim 18, wherein the polypeptide is contacted with the oil for 2 hours.

20. The process of claim 1, comprising contacting the oil with the polypeptide and water, and stirring for from 0.5 to 24 hours, wherein the oil comprises a non-degummed crude oil.

21. The process of claim 1, comprising contacting the oil with the polypeptide, water, and an additional enzyme, and stirring for from 0.5 to 24 hours, wherein the oil comprises a non-degummed crude oil.

22. The process of claim 21, wherein the additional enzyme is selected from the group consisting of PLC, PI-PLC, and combinations thereof.

23. The process of claim 1, comprising contacting the oil with the polypeptide and water, and stirring the resulting oil, wherein the oil comprises a once refined oil.

24. The process of claim 1, further comprising treating the oil with an additional enzyme selected from the group consisting of a phospholipase, a pheophytinase, a pyropheophytinase, a chlorophyllase, and combinations thereof.

25. A process for treating an oil comprising a chlorophyll substrate, the process comprising contacting the oil with a polypeptide having decolorase activity or a composition comprising the polypeptide, water, and an additional enzyme, at a pH of from 4 to 8; and stirring the resulting oil for from 0.5 to 24 hours, wherein the polypeptide is dosed into the oil in an amount of 1 to 50 U/gram oil.

26. The process of claim 25, wherein the additional enzyme is selected from the group consisting of PLC, PI-PLC and combinations thereof.

27. The process of claim 25, further comprising adding a PLA enzyme to the oil following stirring.

28. The process of claim 27, wherein the PLA enzyme is a PLA1 enzyme.

29. The process of claim 28, wherein the oil is stirred for from 1 to 8 hours following addition of the PLA1 enzyme.

* * * * *